US010857036B2

(12) United States Patent
Peli et al.

(10) Patent No.: US 10,857,036 B2
(45) Date of Patent: *Dec. 8, 2020

(54) ACTIVE CONFOCAL IMAGING SYSTEMS AND METHODS FOR VISUAL PROSTHESES

(71) Applicant: The Schepens Eye Research Institute, Inc., Boston, MA (US)

(72) Inventors: Eliezer Peli, Boston, MA (US); Jae-Hyun Jung, Boston, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 125 days.

This patent is subject to a terminal disclaimer.

(21) Appl. No.: 16/183,930

(22) Filed: Nov. 8, 2018

(65) Prior Publication Data
US 2019/0192348 A1 Jun. 27, 2019

Related U.S. Application Data

(63) Continuation of application No. 15/126,775, filed as application No. PCT/US2015/021543 on Mar. 19, 2015, now Pat. No. 10,130,513.
(Continued)

(51) Int. Cl.
*A61N 1/36* (2006.01)
*A61F 9/08* (2006.01)
(Continued)

(52) U.S. Cl.
CPC ............... *A61F 9/08* (2013.01); *A61H 3/061* (2013.01); *A61N 1/0543* (2013.01);
(Continued)

(58) Field of Classification Search
CPC ................ A61F 9/08; A61H 2003/063; A61H 2201/165; A61H 2201/5038;
(Continued)

(56) References Cited

U.S. PATENT DOCUMENTS 5,060,062 A 10/1991 Dotson
5,760,950 A 6/1998 Maly
(Continued)

FOREIGN PATENT DOCUMENTS

WO WO 2002/40095 5/2002
WO WO 2015/143203 9/2015

OTHER PUBLICATIONS

Aloni and Yitzhaky., "Automatic 3D object localization and isolation using computational integral imaging," Appl. Opt., Aug. 2015, 54(22):6717-6724.
(Continued)

*Primary Examiner* — George Manuel
(74) *Attorney, Agent, or Firm* — Fish & Richardson P.C.

(57) ABSTRACT

The disclosure features systems and methods for providing information to a user about the user's environment. The systems feature a detection apparatus configured to obtain image information about the environment, where the image information corresponds to information at multiple distances relative to a position of the user within the environment, and an electronic processor configured to obtain focal plane distance information defining a set of one or more distance values relative to the position of the user within the environment, construct one or more confocal images of the environment from the image information and the set of one or more distance values, wherein each of the one or more confocal images corresponds to a different distance value and includes a set of pixels, and transform the one or more confocal images to form one or more representative images having fewer pixels and a lower dynamic range.

20 Claims, 10 Drawing Sheets

Related U.S. Application Data

(60) Provisional application No. 61/955,698, filed on Mar. 19, 2014.

(51) Int. Cl.
*A61H 3/06* (2006.01)
*A61N 1/05* (2006.01)

(52) U.S. Cl.
CPC .... *A61N 1/36046* (2013.01); *A61H 2003/063* (2013.01); *A61H 2201/165* (2013.01); *A61H 2201/5038* (2013.01); *A61H 2201/5048* (2013.01); *A61H 2201/5084* (2013.01); *A61H 2201/5092* (2013.01); *A61H 2201/5097* (2013.01)

(58) Field of Classification Search
CPC .... A61H 2201/5048; A61H 2201/5084; A61H 2201/5092; A61H 2201/5097; A61H 3/061; A61N 1/0543; A61N 1/36046
See application file for complete search history.

(56) References Cited

U.S. PATENT DOCUMENTS

| | | | |
|---|---|---|---|
| 7,308,314 | B2 | 12/2007 | Havey et al. |
| 7,457,434 | B2 | 11/2008 | Azar |
| 2006/0147197 | A1 | 7/2006 | Spruck et al. |
| 2011/0206291 | A1* | 8/2011 | Kashani ............. A61B 5/14555 382/255 |
| 2012/0242801 | A1 | 9/2012 | Barnes |
| 2014/0009591 | A1 | 1/2014 | Ziemeck et al. |
| 2016/0309137 | A1 | 10/2016 | McNamer et al. |

OTHER PUBLICATIONS

Aloni and Yitzhaky., "Effects of elemental images' quantity on three-dimensional segmentation using computational integral imaging," Appl. Opt., Mar. 2017, 56(8):2132-2140.
Cha et al., "Mobility performance with a pixelized vision system," Vision Research, Jul. 1992, 32(7):1367-1372.
Chen et al., "A quantitative analysis of head movement behaviour during visual acuity assessment under prosthetic vision simulation," Journal of Neural Engineering, Feb. 2007, 4(1):S108-S123.
Davison., "Real-time simultaneous localisation and mapping with a single camera," Proceedings Ninth IEEE International Conference on Computer Vision, Nice, France, 2003, 8 pages.
Gibson et al., "Motion parallax as a determinant of perceived depth," Journal of Experimental Psychology, Jul. 1959, 58(1):40-51.
Harris., "Focusing on Everything: Light-field cameras promise an imaging revolution," IEEE Spectrum, May 2012, 49(5):44-50.
Hartley & Zisserman, "Chapter 6. Camera Model" in Multiple View Geometry in Computer Vision, Second Edition, Cambridge University Press: Cambridge, UK, 2000, 35 pages.
Jung et al., "Active confocal imaging for visual prostheses," Vision Research, Jun. 2015, 111(PB):182-196.
Jung et al., "Reconstruction of three-dimensional occluded object using optical flow and triangular mesh reconstruction in integral imaging," Optics Express, Dec. 2010, 18(25):26373-26387.
PCT International Preliminary Report on Patentability in International Appln. No. PCT/US18/22916, dated Oct. 1, 2019, 7 pages.
PCT International Preliminary Report on Patentability in International Appln. No. PCT/US2015/021543, dated Mar. 19, 2014, 8 pages.
PCT International Search Report and Written Opinion in International Appln. No. PCT/US18/22916, dated Jun. 8, 2018, 13 pages.
U.S. Appl. No. 15/126,775, filed Sep. 16, 2016, Peli & Jung.
Saxena et al., "Depth estimation using monocular and stereo cues," In Proceedings of the 20th International Joint Conference on Artifical Intelligence (IJCAI), Jan. 2007, 7:2197-2203.
Schiller & Tehovnik., "Visual Prosthesis," Perception, Oct. 2008, 37(10):1529-1559.
Shin et al., "Optical flow-based real-time object tracking using non-prior training active feature model," Real-Time Imaging, Jun. 2005, 11(3):204-218.
Sun et al., "Secrets of optical flow estimation and their principles," in Proceedings of IEEE Conference on Computer Vision and Pattern Recognition (IEEE, 2010), 2432-2439.
Zhou et al., "Object tracking using SIFT features and mean shift," Computer Vision and Image Understanding, Mar. 2009, 113(3):345-352.
Aloni & Yitzhaky, Detection of object existence from a single reconstructed plane obtained by integral imaging, IEEE Photonics Technology Letters, 2014, 26(7), 726-728.
Goldstein et al., "Medical image communication using halftone algorithms," Proceedings of the Society of Photo-Optical Instrumentation Engineers, 1987, 845: 413-418.
International Search Report, Application No. PCT/US2015/021543, dated Jun. 9, 2015.
Lange and Seitz, "Solid-state time-of-flight range camera," IEEE Journal of Quantum Electronics, 2001, 37(3), 390-397.
Levoy et al., "Synthetic aperture confocal imaging," ACM SIGGRAPH 2004 Papers, 2004, pp. 825-834.
Lieby et al., "Substituting depth for intensity and real-time phosphene rendering: Visual navigation under low vision conditions," EMBC, 2011, 8017-8020.
Mallat, "Multifrequency channel decompositions of images and the wavelet models," IEEE, 1989,. 37(12), 2091-2110.
McCarthy et al., "Ground surface segmentation for navigation with a low resolution visual prosthesis," Proceedings of the Annual International Conference of the IEEE Engineering in Medicine and Biology Society, 2011, 4457-4460.
Peli and Lahav, "Drusen measurements from fundus photographs using computerized image analysis," Ophthalmology, 1986, 93(12), 1575-1580.
Peli, "Simple 1-D enhancement for head-mounted low vision aid," Visual Impairment Research, 1999, 1(1): 3-10.
Stern and Javidi, "Three dimensional sensing, visualization, and processing using integral imaging," Proceedings of IEEE, Special Issue on 3D Technologies for Imaging and Display, 22006, 94(3): 591-607.

* cited by examiner

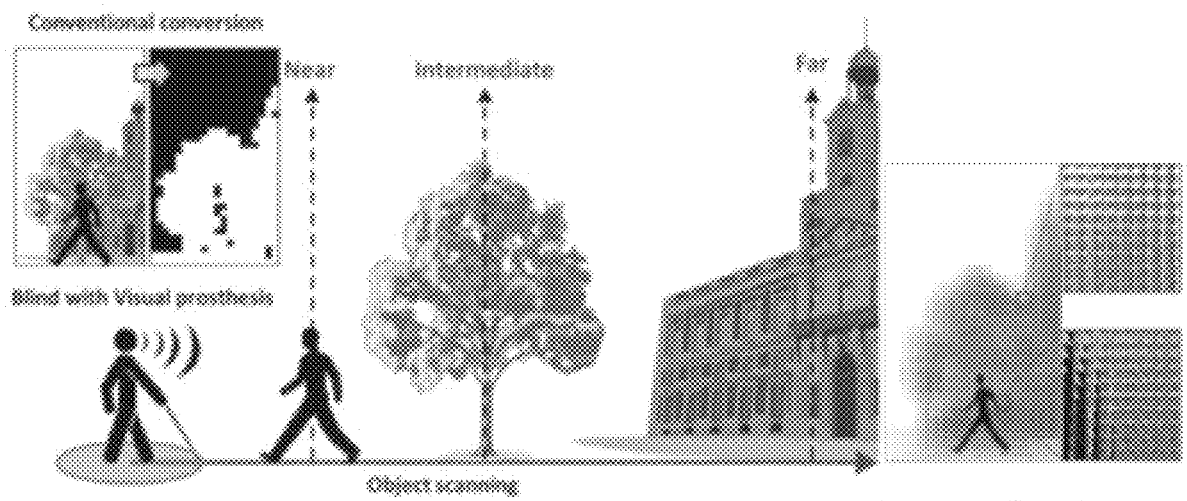
FIG. 4A
FIG. 4B
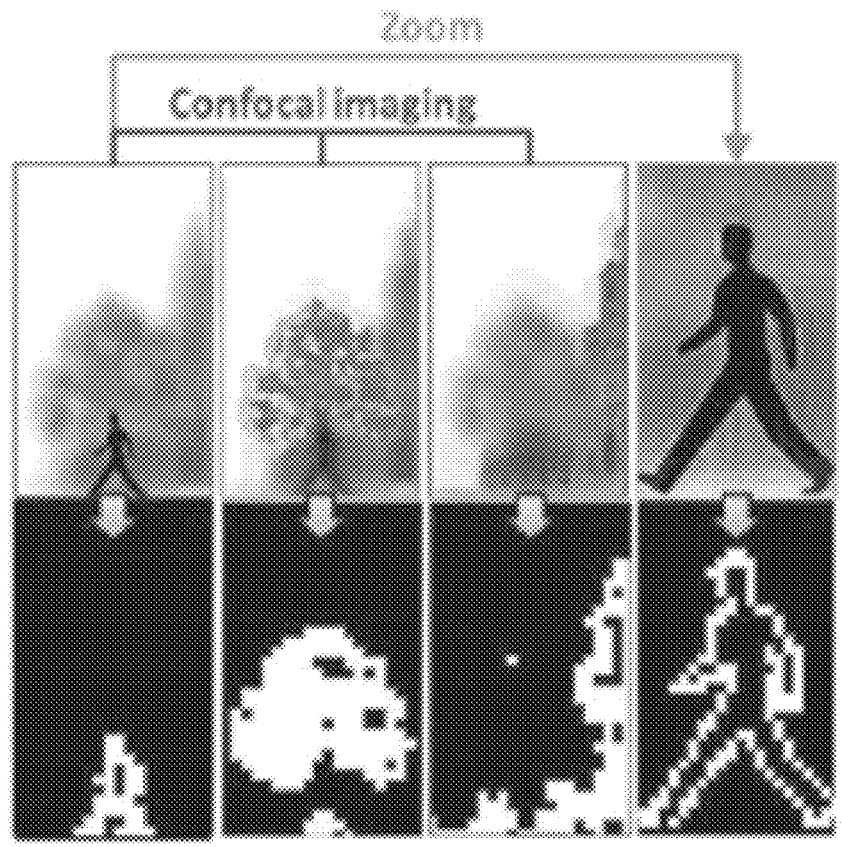
FIG. 4C   FIG. 4D   FIG. 4E   FIG. 4F

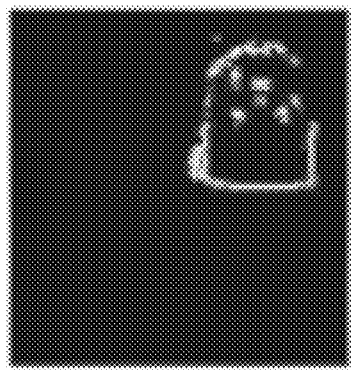 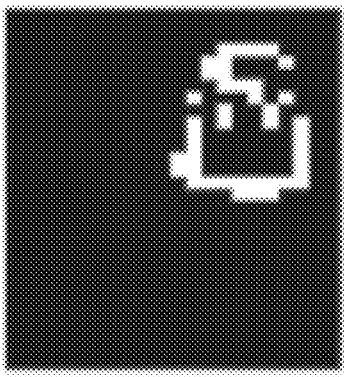 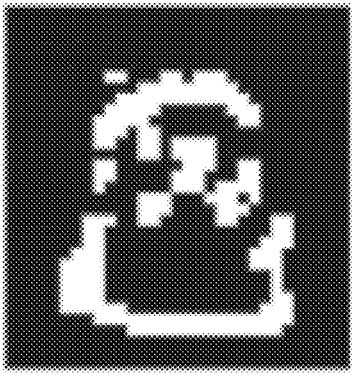
FIG. 5A  FIG. 5B  FIG. 5C
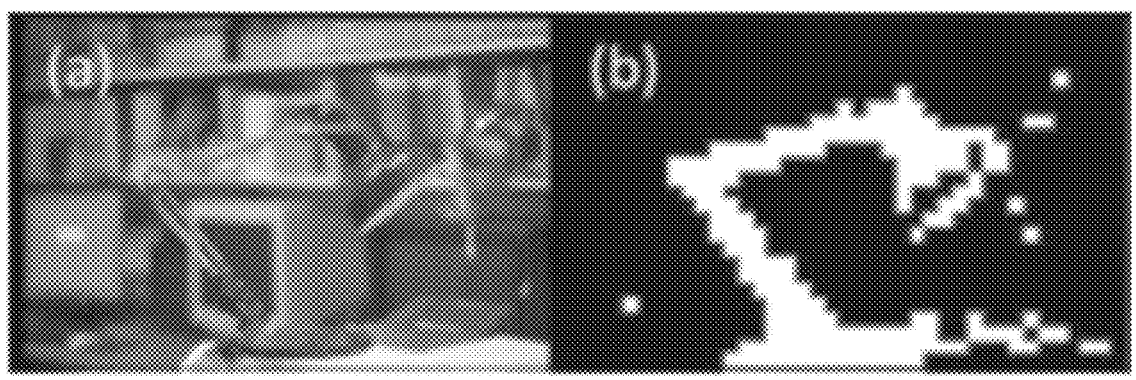
FIG. 6A  FIG. 6B
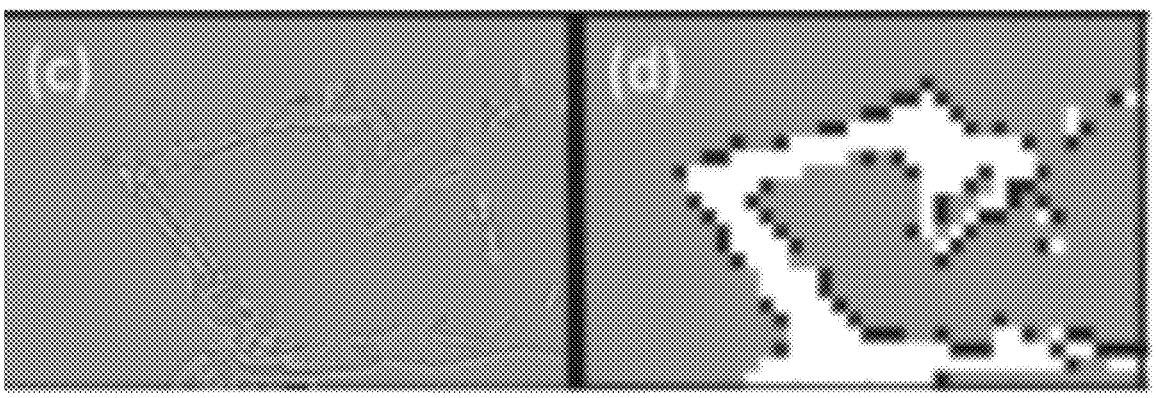
FIG. 6C  FIG. 6D

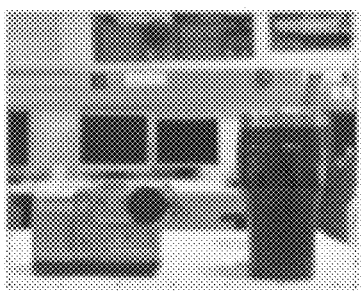 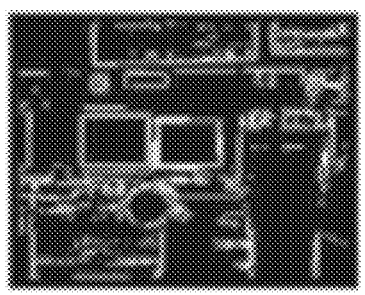 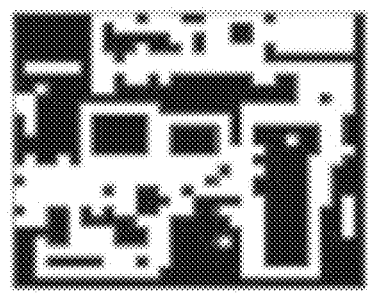
FIG. 7A    FIG. 7B    FIG. 7C
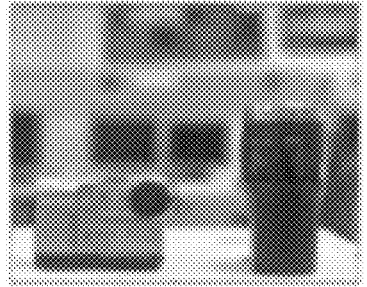 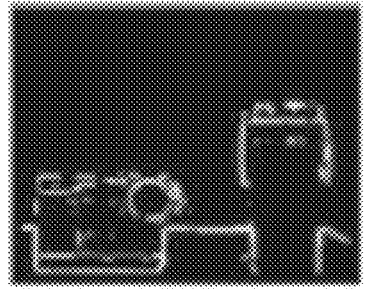 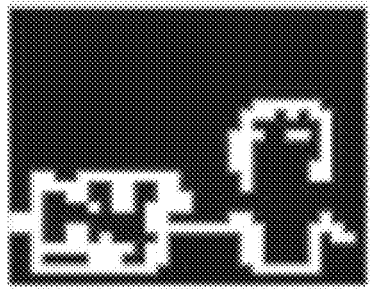
FIG. 7D    FIG. 7E    FIG. 7F
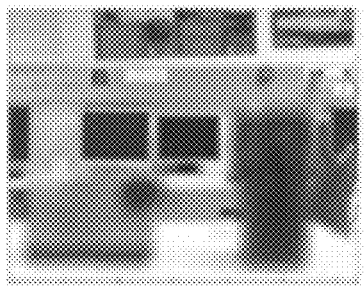 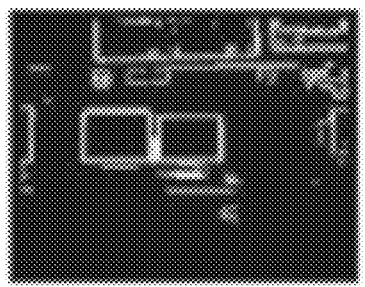 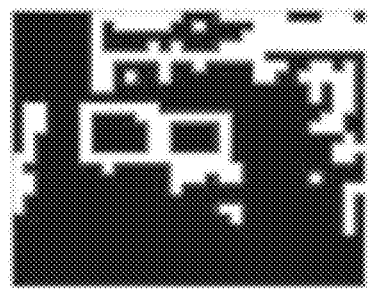
FIG. 7G    FIG. 7H    FIG. 7I
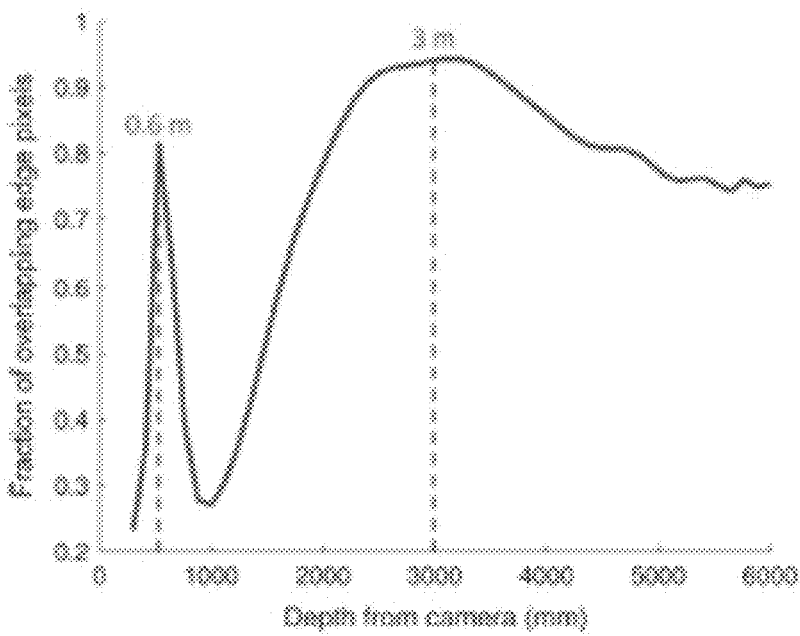
FIG. 7J

ACTIVE CONFOCAL IMAGING SYSTEMS AND METHODS FOR VISUAL PROSTHESES

CROSS-REFERENCE TO RELATED APPLICATIONS

This application is a continuation of U.S. patent application Ser. No. 15/126,775, filed Sep. 16, 2016, which is a 371 U.S. National Phase Application of PCT Application No. PCT/US2015/021543, filed on Mar. 19, 2015, which claims priority to U.S. Provisional Patent Application No. 61/955,698, filed on Mar. 19, 2014, the contents of which are incorporated herein by reference in their entirety.

STATEMENT AS TO FEDERALLY SPONSORED RESEARCH

This invention was made with Government support under NIH grant number R01EY05957. The Government has certain rights in the invention.

TECHNICAL FIELD

This disclosure relates to imaging systems and methods to address visual impairment.

BACKGROUND

According to the World Health Organization, an estimated 39 million people worldwide are blind. In the United States, 1.2 million people are legally blind and ~10% of them are functionally blind. Their numbers are projected to grow in the coming decades. Although blind people can access text through braille and text-to-speech, mobility indoors and outside is limited, dangerous, and largely depends on the long cane. Blindness also limits numerous other activities of daily living, particularly tasks requiring visual search and object recognition. As a result, many pursuits (vocational and social) are limited, especially for the acquired blind whose blindness occurs in adulthood. Restoration of vision through prostheses is expected to address many of these difficulties.

SUMMARY

This disclosure features systems and methods for providing information about a user's environment to the user. In particular, for vision-impaired users, e.g., severely vision-impaired (e.g., totally blind or functionally blind) users, the information can be provided in the form of image data that is converted to electrical signals and delivered to a visual prosthesis such as retinal implants in the user's eye that use additional camera systems. Information can also be provided in the form of other signals, including haptic signals (e.g., vibrations, movements, and other tactile signals) and auditory signals. For some prosthetics, the information can include visual or nonvisual information (e.g., infrared images) provided through a head-mounted display. Visual prostheses using additional camera system can use the featured systems.

The systems and methods disclosed herein generally apply confocal imaging techniques to generate images of the user's environment that correspond to images at selected distances from the user's position within his or her environment. As such, the images of the user's environment represent focal planes at particular distances relative to the user's position (e.g., focal planes with a narrow depth of field). Because the images are confocal in nature, objects positioned within a plane corresponding to the particular distances are well focused, whereas objects in other planes appear blurred. The blurring of these out-of-plane objects allows the systems and methods to selectively provide to the user information about the in-plane objects and suppress information from other distances/focal planes.

The systems and methods disclosed herein apply image processing techniques to separate image information corresponding to in-plane objects (e.g., objects at selected distances or within particular focal planes relative to the user's position) from out-of-plane/out-of focus objects to effectively suppress and remove clutter, background clutter. The image information provided to the user therefore represents largely only the in-plane objects, and is presented in a compressed (e.g., reduced resolution and reduced dynamic range) format suitable for retinal implants or other visual prostheses, including sensory substitution devices. In some cases, the user can select the image information to be shown to the user by freely scanning and traversing through confocal images and then selecting the focal plane that includes the object of interest.

In a first aspect, the disclosure features systems and methods for providing information to a user about the user's environment, the systems featuring a detection apparatus configured to obtain image information about the environment, where the image information corresponds to information at multiple distances relative to a position of the user within the environment, and an electronic processor configured to: obtain focal plane distance information defining a set of one or more distance values relative to the position of the user within the environment; construct one or more confocal images of the environment from the image information and the set of one or more distance values, where each of the one or more confocal images corresponds to a different distance value and comprises a set of pixels; and transform the one or more confocal images to form one or more representative images, where each representative image corresponds to one of the confocal images and is compressed into fewer pixels and a lower dynamic range than the set of pixels and a dynamic range of the corresponding confocal image.

Embodiments of the systems can include any one or more of the following features.

The detection apparatus can include a light-field imaging system as well as any other depth cameras (e.g., time-of-flight, structured light, stereo-, or multiple-cameras) that can generate three-dimensional distance information. In the case of depth cameras, after a depth map is generated, objects in a selected depth plane are included and objects in other depth planes are removed from the depth map. In some cases, a confocal image can be generated with other imaging systems (e.g., a stereo imaging system). The detection apparatus can include a detector and an array of lenses in light-field imaging, and each lens can be positioned to image light representing a different image of the environment onto the detector. The detector can include at least one of a charge-coupled device (CCD) and a complementary metal-oxide semiconductor (CMOS)-based device. The array of lenses can be positioned relative to the detector so that each lens in the array directs light corresponding to a different image onto a different portion of the detector. Each lens and each portion of the detector capture different angular and spatial light information (e.g., a light-field), view and perspective, of a three-dimensional scene in front of the features systems. Light-field information can generate confocal images from the captured information at any selected focal plane.

The electronic processor can be configured to construct the one or more confocal images by combining portions of the image information that correspond to images formed on the detector by different lenses in the array (e.g., elemental image array). The one or more confocal images can include at least 3 confocal images (e.g., at least 4 confocal images, at least 5 confocal images, at least 7 confocal images, at least 10 confocal images, at least 12 confocal images, or many tens of confocal images).

The systems can operate in one of several modes, including a free-search mode, a confocal extension mode, and an obstacle avoidance mode. In the free-search mode, the focal plane distance information can be selected by the user. In the confocal-extension mode, the focal plane distance information can be selected based on a location of a body part of the user detected by the detection apparatus. In the obstacle avoidance mode, the focal plane distance information can be a pre-selected depth range from the position of the user.

The image information can include a set of confocal images each corresponding to a focal plane at a different distance relative to the position of the user. The focal plane distance information can include a range of distance values bounded by a minimum distance value. The focal plane distance information can include a range of distance values bounded by a maximum distance value.

The electronic processor can be configured to obtain the focal plane distance information by determining an operating mode associated with the system. The electronic processor can be configured to transform the one or more confocal images by performing an edge detection analysis on the one or more confocal images. In some embodiment, if the dynamic range of the visual prostheses supports multi-level dynamic range, bipolar edge filtering can be used to interpret contrast differences. The edges can be binary edges or can be bipolar edges containing at least 3 gray levels. The electronic processor can also be configured to transform the one or more confocal images by converting the one or more confocal images to halftone images. The electronic processor can be configured to convert the one or more representative images into electrical signals, and to transmit the electrical signals to a visual prosthesis worn by the user.

The systems can include an input interface configured to receive input information from the user and to transmit the input information to the electronic processor. The input interface can include a controller mounted to a cane. The input interface can include a voice-activated interface. The electronic processor can be configured to obtain the focal plane distance information from the user through the input interface.

The electronic processor can be configured to transform the one or more confocal images to form the one or more representative images by removing, from each one of the one or more confocal images, information corresponding to objects that are not in focus in a focal plane corresponding to a distance value associated with the confocal image.

Embodiments of the systems can also include any of the other features disclosed herein, including features disclosed in connection with different embodiments, in any combination as appropriate.

In another aspect, the disclosure features methods for providing information to a user about the user's environment, the methods including obtaining image information about the environment, where the image information corresponds to information at multiple distances relative to a position of the user within the environment; obtaining focal plane distance information defining a set of one or more distance values relative to the position of the user within the environment; constructing one or more confocal images of the environment from the image information and the set of one or more distance values, where each of the one or more confocal images corresponds to a different one of the distance values and includes a set of pixels; and transforming the one or more confocal images to form one or more representative images, where each representative image corresponds to one of the confocal images and includes fewer pixels and a lower dynamic range than the set of pixels and a dynamic range of the corresponding confocal image.

Embodiments of the methods can include any one or more of the following features.

Obtaining image information about the environment can include using a confocal imaging system to measure the image information. Obtaining image information about the environment can include using an array of lenses to image light onto a detector. Each lens in the array can direct light corresponding to a different image onto a different portion of the detector.

The methods can include constructing the one or more confocal images by combining portions of the image information that correspond to images formed on the detector by different lenses in the array. The one or more confocal images can include at least 3 confocal images (e.g., at least 4 confocal images, at least 5 confocal images, at least 7 confocal images, at least 10 confocal images, at least 12 confocal images. The image information can include a set of confocal images, each corresponding to a focal plane at a different distance relative to the position of the user.

In some cases, the one or more confocal images can be constructed by overlapping at least 2 elemental images (e.g., at least 4 elemental images, at least 5 elemental images, at least 7 elemental images, at least 10 elemental images, at least 12 elemental images, or many tens of elemental images). The image information can include a set of confocal images, each confocal image comprising overlapping elemental images formed on the detector by different lenses in the array.

The focal plane distance information can include a range of distance values bounded by a minimum distance value. The focal plane distance information can include a range of distance values bounded by a maximum distance value. The methods can include obtaining the focal plane distance information by determining an operating mode associated with the system.

The methods can include transforming the one or more confocal images by performing an edge detection analysis on the one or more confocal images. The methods can include transforming the one or more confocal images by converting the one or more confocal images to halftone images. In some examples, the methods include transforming the one or more confocal images by converting the one or more confocal images to binary, bipolar, or multi-level edge images. The methods can include converting the one or more representative images into electrical signals, and transmitting the electrical signals to a visual prosthesis worn by the user. The methods can include obtaining the focal plane distance information from the user through an input interface.

The methods can include transforming the one or more confocal images to form the one or more representative images by removing, from each one of the one or more confocal images, information corresponding to objects that are not in focus in a selected focal plane/range corresponding to a distance value associated with the confocal image.

The methods can include selecting at least one of a free-search mode, a confocal extension mode, and an obstacle avoidance mode. In the free-search mode, the focal plane distance information can be selected by the user. In the confocal-extension mode, the focal plane distance information can be selected based on a location of a body part of the user detected by the detection apparatus. In the obstacle avoidance mode, the focal plane distance information can be a pre-selected depth range from the position of the user.

The image information can include a set of confocal images each corresponding to a focal plane at a different distance relative to the position of the user. The focal plane distance information can include a range of distance values bounded by a minimum distance value. The focal plane distance information can include a range of distance values bounded by a maximum distance value.

Embodiments of the methods can also include all of the other features or steps disclosed herein, including features or steps disclosed in connection with different embodiments, in any combination as appropriate.

In the present disclosure, various embodiments are discussed for purposes of illustration. In general, however, the features and steps associated with the various embodiments are not specific to those embodiments unless otherwise noted, and can be combined with other features and steps. Accordingly, the present disclosure should not be understood to be limited to the specific combinations of features and steps described, but also encompasses other combinations of the features and steps disclosed herein, except where indicated otherwise.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIG. 4A is a schematic diagram showing the environment of a blind person, including objects located at various distances relative to the position of the blind person.

FIG. 4B is a schematic diagram showing three-dimensional image information for the blind person's environment of FIG. 4A, obtained using a lens array and detector.

FIG. 4C is a confocal image corresponding to a focal plane located at a distance of an approaching person relative to the blind person of FIG. 4A, and a binary edge representative image derived from the confocal image.

FIG. 4D is a confocal image corresponding to a focal plane located at a distance of a tree relative to the blind person of FIG. 4A, and a binary edge representative image derived from the confocal image.

FIG. 4E is a confocal image corresponding to a focal plane located at a distance of a building relative to the blind person of FIG. 4A, and a binary edge representative image derived from the confocal image.

FIG. 4F is a zoomed confocal image derived from the confocal image of FIG. 4C, and a representative binary edge image derived from the zoomed confocal image.

FIG. 5A is a representative binary edge image of the backpack shown in the confocal image of FIG. 2C.

FIG. 5B is a compressed, lower-resolution version of the image of FIG. 5A.

FIG. 5C is a compressed, lower-resolution version of a zoomed version of the image of FIG. 5A.

FIG. 6A is a confocal image showing a desk lamp at a near distance from a camera and a complex background at a far distance from the camera.

FIG. 6B is a compressed binary edge representative image derived from the confocal image of FIG. 6A.

FIG. 6C is an image generated from a bipolar edge filtering technique. The image shows a desk lamp at a near distance from a camera and a complex background at a far distance from the camera.

FIG. 6D is a compressed representative bipolar edge image derived from the image of FIG. 6C.

FIGS. 7A-7C are non-confocal images and binary edge representations of a scene.

FIGS. 7D-7F are confocal images and binary edge representations of the scene of FIGS. 7A-7C at a first confocal distance.

FIGS. 7G-7I are confocal images and binary edge representations of the scene of FIGS. 7A-7C at a second confocal distance.

FIG. 7J is a graph of a fraction of overlapping edge pixels measured against a depth from a camera imaging the scene of FIGS. 7A-7C.

Like reference symbols in the various drawings indicate like elements.

DETAILED DESCRIPTION

Imaging Systems

Figure 1:
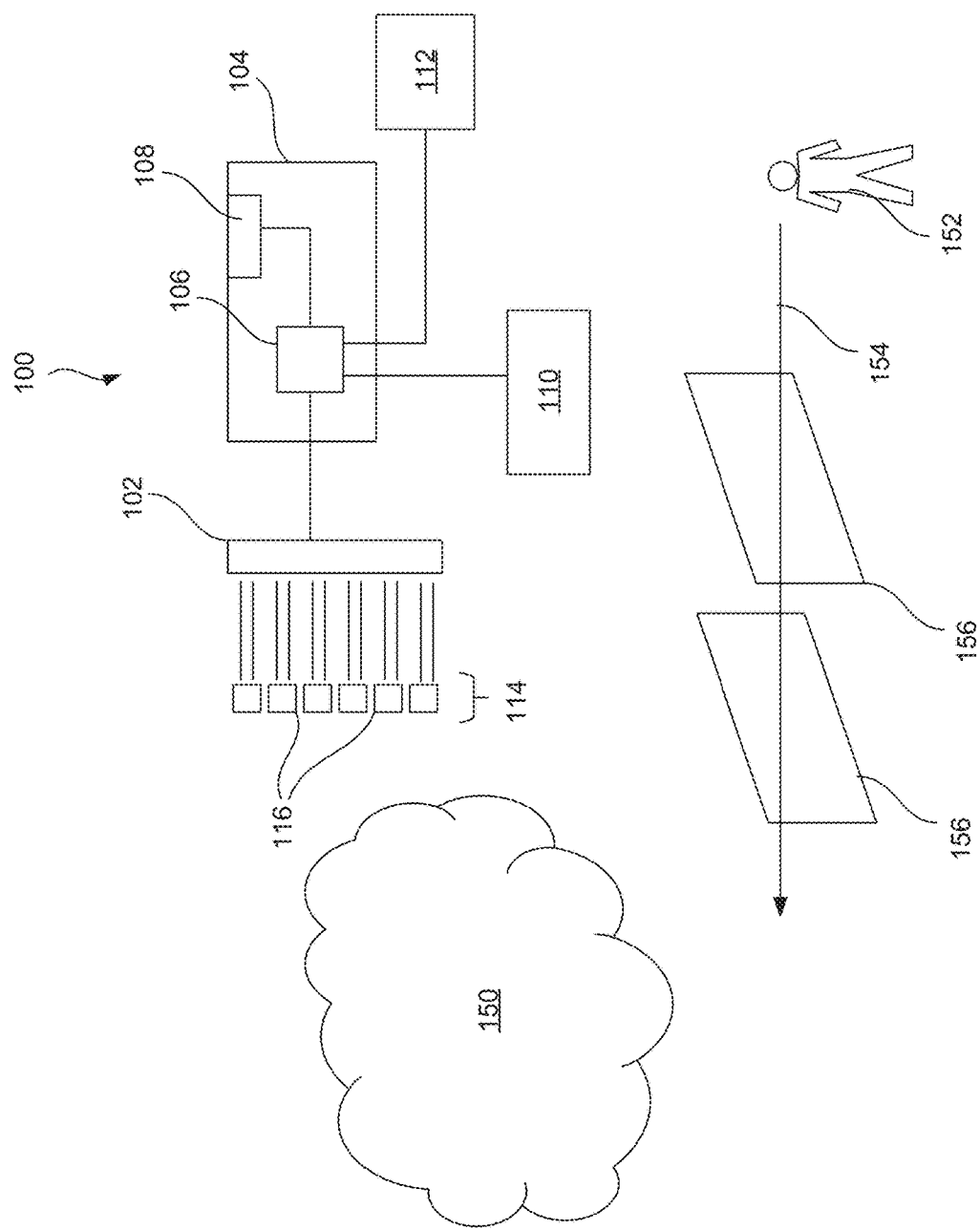
FIG. 1 is a schematic diagram of an embodiment of an active confocal imaging system.

FIG. 1 is a schematic diagram showing an embodiment of an imaging system 100 for providing information about a user's environment to a user. As discussed above, imaging system 100 is particularly well suited to provide information to a vision-impaired user. However, more generally, system 100 can be used to provide information in a variety of applications where a reduced-resolution representation of the user's environment is useful. The system 100 can be further implemented into environments with low-lighting and poor visual conditions (e.g., total darkness, dense fog, underwater, or smoke conditions).

System 100 includes a detector 102 coupled to a control unit 104. Control unit 104 includes an electronic processor 106 and, optionally, a signal transmitter 108 coupled to processor 106. Also included in system 100 are an optional input interface 110 and an optional output device 112, both of which are coupled to electronic processor 106.

In general, detector 102 is configured to obtain image information about the environment 150 of a user of system 100. In general, the image information corresponds to information in focal planes at multiple distances relative to a position of the user 152 within the environment. As shown schematically in FIG. 1, the image information corresponds to information obtained at one or more focal planes 156 positioned along axis 154, which extends in a direction outward from user 152.

In general, in this embodiment system 100 corresponds to a confocal imaging system. Conventional confocal imaging systems acquire images that each correspond to a relatively shallow depth of focus (e.g., include contributions from objects located within or very close to a nominal focal plane), while contributions from objects located outside the depth of focus range are reduced by blur or even suppressed entirely. Conventional camera lenses can have a setting for an f-stop. To achieve a narrow depth of focus, the f-stop (e.g., f-number or focal length divided by aperture size) can be set to a low value. However, lenses having low f-stop settings can be bulky and heavy, thus rendering them difficult to implement in confocal imaging systems.

A conventional camera and a commercial light-field camera having similar specifications can have varying depths of focus. The conventional camera can have a wider depth of focus, limiting its use in confocal imaging, which utilizes narrower depths of focus. On the other hand, a light-field camera can capture an image in one exposure/frame and generate multiple confocal images through rapid computation without the mechanical movements required for a conventional camera. The light-field camera can generate confocal images with a depth of focus narrower than a single narrow depth of focus lens. Whereas the depth of focus in a single lens is limited by the designed f-number, the f-number of a light-field camera can be controlled by the synthesized aperture of the light-field camera instead of the physical aperture of a single camera lens. With a multiple-camera array, the same lens can create a much smaller f-number using a synthetic aperture determined by the distance between cameras. Systems and methods related to light-field cameras are further described in, for example, Levoy et al., "Synthetic aperture confocal imaging," published in 2004, (*ACM SIGGRAPH* 2004 *papers*, Los Angeles, Calif.: ACM, pages 825-834) and Ng et al., "Light field photography with a hand-held plenoptic camera," Stanford University (2005), the contents of which are incorporated in their entireties. Accordingly, in some embodiments, the image information acquired by system 100 can include a set of confocal images of environment 150 acquired by, for example, a light-field camera. Each of the images captured by the camera can correspond to a different nominal focal plane located at a different distance along axis 154 relative to user 152.

In certain embodiments, system 100 can obtain image information corresponding to multiple focal planes at different distances from user 152 in a single image frame. To obtain the image information in this manner, system 100 can include a two-dimensional array 114 of lenses 116, as shown in FIG. 1. Each of the lenses in array 114 captures an elemental image of environment 150 from a slightly different perspective. Each of the lenses 116 directs radiation, e.g., light, that forms the image it captures onto a different spatial region of detector 102. For example, as will be described below in more detail, FIG. 4A is captured as shown in FIG. 4B through the lens array 114. In some implementations, the radiation is visible light. In other cases, the radiation can be infrared light or other radiation that can interact with and image the environment. Information (e.g., pixel intensity values) from different regions of detector 102 (which can include, for example, an array of detection elements) can then be combined to yield individual confocal images of environment 150 that correspond to particular focal planes at different distances along axis 154, relative to the position of detector 102. In cases where the detector 102 includes an array of detection elements, the detector 102 can generate an array of elemental images, where each elemental image corresponds to an image generated by a detection element in the array of the detection elements. Because detector 102 is generally worn or carried by user 152, the focal planes are also located at different distances along axis 154 relative to the position of user 152.

A variety of different types of detection elements can be used in detector 102 to obtain the image information. In some embodiments, for example, detector 102 includes a charge-coupled device (CCD) array. In certain embodiments, detector 102 is a complementary metal-oxide semiconductor (CMOS) device. Detector 102 can be integrated within a camera, for example.

System 100 can also include a variety of other imaging components. For example, system 100 can include one or more lenses, filters, beam splitters, diffractive elements, apertures, spatial modulators, and mirrors. As discussed above, in some embodiments, system 100 includes a two-dimensional array of lenses positioned so that each lens in the array directs light to a different spatial region of detector 102. The two-dimensional array can be a square array, a rectangular array, a hexagonal array, a circular array, or another type of array. Further, in some embodiments, each of the lenses in the array are of the same type (e.g., formed from the same material, and/or have the same shape and focusing properties). Alternatively, in certain embodiments, array 114 can include more than one different type of lenses. The different types of lenses can have different optical properties (e.g., different focal lengths), different shapes, and/or can be formed from different materials, for example. While the system 100 has been described as directing and re-directing light, in other embodiments, the system 100 can emit other radiation or signals that can interact with the environment and detect features of the environment. For example, the system 100 can emit radiofrequency waves, ultrasonic waves, infrared light, or other waveforms. The system 100 can also have magnifying or minifying optics (lens set) in front of the array 114 to enlarge or shrink the images formed by the system 100.

As shown in FIG. 1, system 100 can optionally include a signal transmitter 108 coupled to electronic processor 106. In some embodiments, signal transmitter 108 is configured to transmit electrical signals (wirelessly or through conductors) to a visual prosthesis worn by user of system. In general, system 100 can be used with a wide variety of different visual prostheses, and signal transmitter 108 can be configured to deliver electrical signals that are compatible with each such prosthesis. As one example, signal transmitter 108 can transmit signals that are compatible with retinal implants positioned within an eye of the user.

During operation of system 100, electronic processor 106 generates one or more images for transmission to a visual prosthesis. The images are then converted by processor 106 and/or signal transmitter 108 into electrical signals suitable for the prosthesis, and transmitted by signal transmitter 108 to the prosthesis. Where system 100 does not include transmitter 108, images can be converted into electrical signals by processor 106, which then transmits the signals directly to the prosthesis.

System 100 can optionally include an input interface 110. Input interface 110 allows the user to transmit information and instructions to system 100, which are then used to adjust the operating parameters of system 100. A variety of different interfaces can be used, including touch-sensitive interfaces, interfaces that incorporate various tactile controls such as buttons, switches, and knobs, and voice-activated interfaces that include a microphone for receiving auditory instructions from the user. The system 100 can include wireless control (e.g., Bluetooth or WiFi) to allow the user to control the system 100 without the use of a direct wired connection. To allow the user to direct system 100 to particular objects within the user's environment, input interface 110 can include sensors such as gyroscopes, accelerometers, touch pads, and knobs that allow the user to select objects through gesture-based movements such as nodding of the head and hand motions.

Input interface 110 can be mounted in a variety of ways to permit the user to conveniently and accurately deliver information and instructions to system 100. In some embodiments, for example, input interface 110 can be integrated into the handle of a long cane carried by the blind user, allowing the user to deliver instructions to the system with relatively slight, unobtrusive hand/finger movements. In some embodiments, input interface 110 can be integrated into one or more articles of clothing or jewelry (e.g., a ring, bracelet, glove, necklace, pin, pendant, or eyeglass frames).

System 100 can also optionally include an output device 112. Output device 112 is generally configured to convey information to the user in the form of warning or alerting signals that draw the user's attention to objects in the user's environment. Such signals can be delivered to the user via output device 112 when, for example, an object closely approaches the user, or when an object is detected. A variety of different signals can be provided to the user, including for example tactile signals and auditory signals. Accordingly, output device 112 can be implemented in variety of ways depending upon the nature of the signals to be delivered. In some embodiments, output device 112 can include a vibrating annunciator or another device configured to deliver tactile signals to the user. In certain embodiments, output device 112 can include a speaker or other sound generating device for delivering auditory signals to the user. For example, bone conducting speakers are well suited for such applications, as they leave the natural hearing of a vision-impaired user unimpeded.

Image Generation and Processing

Various prosthetic devices for vision substitution have been proposed. Each of these systems uses a video camera to acquire one or more images of the user's environment, and then converts the high resolution image(s) captured into a compressed format that can be conveyed by the system to the sensory organ.

However, the utility of current and foreseeable visual prostheses is limited due to low resolution, low dynamic range (the number of displayable gray levels), and limited visual field. For example, the resolution of the Argus II retinal implant (available from Second Sight Medical Products, Sylmar, Calif.) is 60 (10×6) electrodes (e.g., 60 pixels), and is expected to be improved to only about 1000 electrodes (e.g., 1000 pixels) in subsequent versions. Similar limitations apply to most sensory substitution devices, for example, the BrainPort® V100 (available from Wicab, Middleton, Wis.) has only 400 electrodes (20×20).

The dynamic range of most prostheses is limited to two (on and off) or at most 3 or 4 levels. The visual field of retinal and cortical prostheses is on the order of 10°, half the field diameter that qualifies as legal blindness, and with a visual acuity of less than 20/1200. The mean acuity score with the BrainPort was reported as only 20/5000. With these limitations, reading even a short word using conventional visual prostheses typically requires minutes, and interpreting a natural image or a scene while walking is enormously difficult.

The performance of these visual prostheses may be improved by an increase in the resolution. However, in addition to technical barriers relating to electrode implementation, biological limitations of the interactions between the sensing organ and the stimulator bound the likely possible resolution. Even if the electrode density is increased, it is unlikely that the perception increase is proportional to the increase in density because crosstalk between electrodes may increase and limit improvement in effective resolution. For example, crosstalk between closely-spaced electrodes can limit an electrode pitch to about 50 μm. Further, the perceived dynamic range of each electrode typically varies, and so even if the theoretical dynamic range has 8 levels and each electrode is calibrated individually, the effective dynamic range generally will not increase proportionally.

The methods and systems disclosed herein implement active image acquisition and processing to generate confocal images of the user's environment, where each confocal image corresponds to focal plane at a particular distance relative to the user's position within his or her environment. The new systems provide active confocal imaging in three stages: confocal image generation, confocal de-cluttering, and image compression into a format suitable for a visual prosthesis.

Each of the confocal images focuses on objects in a particular focal plane (e.g., distance from the user) at a time, and blurs objects and other features of the environment positioned at other distances from the user. With this confocal capability, image processing can identify and remove the blurred pixels and thus suppress the "crowding" resulting from clutter by images of abutting objects located in planes at other distances. The user can actively select distances and objects of interest based on the information derived from the confocal images, in addition to (laterally and vertically) scanning the field-of-view of the imaging system. Further, the user—by issuing appropriate instructions to the system—can zoom in on detected/selected objects for better detail. As a result, the systems and methods disclosed herein can improve the functionality of most visual prostheses and thus accelerate their development and adoption.

Effective compression of information acquired by a detector (e.g., detector 102) to match the limited resolution and dynamic range of a prosthetic system is important to allow information to be delivered to the user, e.g., to match the biological sensor capabilities. Images acquired by conventional imaging systems have proved to be difficult to interpret, even when simulated compressed images were examined with normal vision. While prosthetic systems have demonstrated some success in "clean" laboratory settings without the background clutter that plagues real-world images, performance severely declined when similar recognition tasks were attempted in a natural room environment. Performance on the same tasks improved substantially by blocking the natural environment background clutter.

Reducing the crowding effect of the background clutter can be achieved by focusing on target objects (e.g., objects that are in focus in focal planes at selected distances from the detector and/or user) and reducing contributions from, or even suppressing entirely, contributions to image information that arise from objects and other features in focal planes at other distances. Confocal imaging technology and/or depth-segmentation based imaging can accomplish this.

Confocal Image Generation, De-Cluttering, and Compression Using Binary Edge Filtering Conventional technologies for depth-based imaging and computer vision segmentation suffer from a variety of deficiencies when applied to applications involving visual prostheses. For example, such technologies may not be suitable for use outdoors, where sunlight interferes with infra-red based depth measuring systems. Segmentation methods can be prone to errors near the edges of objects, where reducing or suppressing crowding is most important.

To achieve the acquisition of improved distance-based image information about the user's environment, the methods and systems disclosed herein can use confocal imaging techniques. In general, the methods and systems can be implemented using any imaging technique that provides image information that includes confocal images corresponding to focal planes positioned at selected distances from a detector, or from which confocal images can be constructed. The following discussions focus on several implementations that use, for example, an array of lenses to acquire light field information from which the confocal imaging information can be easily obtained. However, it should be appreciated that other confocal imaging techniques (e.g., structured light imaging, time-of-flight depth measurements, and stereo imaging) can also be used. Stereo imaging (using limited light-field imaging), for example, can include the use of two lenslet sensors spaced far apart from one another.

While a light-field camera is described above, it should be understood that these other cameras can be suitable for implementing the methods described herein. A structured-light camera or time-of-flight camera are types of depth cameras that can be helpful in segmenting an object of interest from the background. A stereo camera, which uses multiple views, can provide a multi-dimensional perspective of a scene. The depth cameras and stereo cameras can therefore alternatively be used to obtain 3D distance information (e.g., depth maps) of a scene. Depth cameras, stereo cameras, and other cameras that can be used for the techniques described herein are further described in Lieby, P., Barnes, N., McCarthy, C., Nianjun, L., Dennett, H., Walker, J. G., Botea, V., and Scott, A. F., "Substituting depth for intensity and real-time phosphene rendering: Visual navigation under low vision conditions," published in 2011; McCarthy, C., Barnes, N., and Lieby, P., "Ground surface segmentation for navigation with a low resolution visual prosthesis," published in 2011 (Proceedings of the Annual International Conference of the IEEE Engineering in Medicine and Biology Society, 4457-4460); Li, W. H., "Wearable computer vision systems for a cortical visual prosthesis," published in 2013 (In Proceedings of the IEEE International Conference on Computer Vision (ICCV) workshops); and Lange, R. and Seitz, P., "Solid-state time-of-flight range camera," published in 2001 (IEEE Journal of Quantum Electronics, 37(3), 390-397), the contents of which are incorporated herein in their entireties.

Figure 2A:
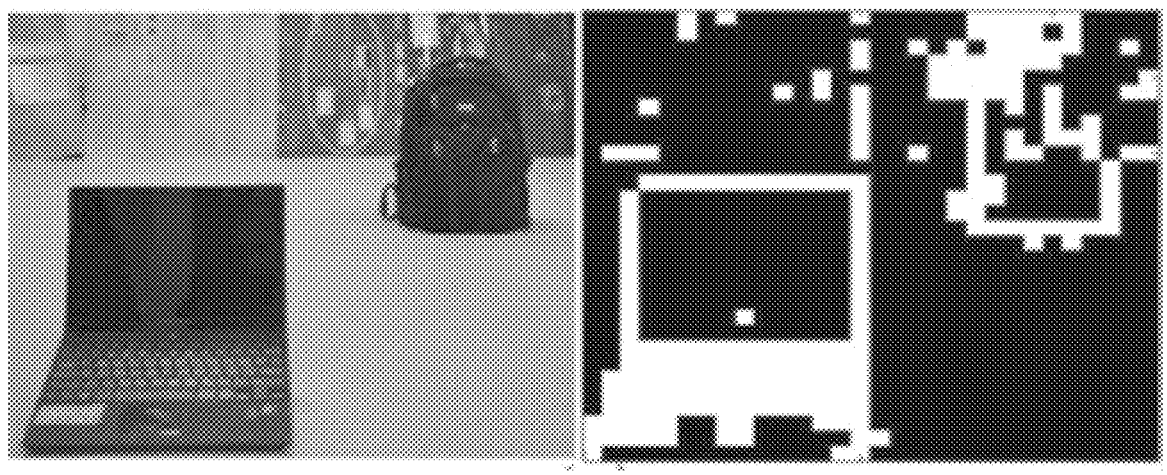
FIG. 2A is a non-confocal image showing a laptop and backpack located at different distances from a camera, and a compressed binary edge representative image derived from the non-confocal image.

In the image of FIG. 2A, a laptop and backpack are located at 1 m and 2 m from a detector (e.g., a light-field camera), respectively, with a complex background at about 3 m away overlapping the upper region of the backpack. An image acquired using a conventional camera (resolution 500×655 pixels) focuses all objects within the camera's depth of field, as shown in the left image. In the representative binary edge image on the right, which is derived from the left image by binary edge filtering and compressing the left image down to a resolution of 30×30 pixels at binary levels (e.g., 2 grey levels), it is difficult to recognize the backpack due to interference from background clutter.

Figure 2B:
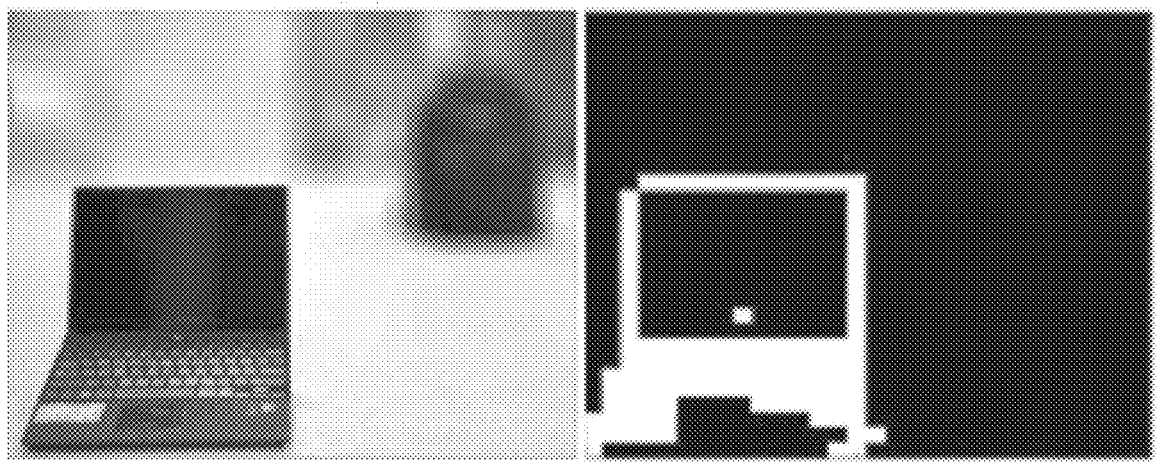
FIG. 2B is a confocal image corresponding to a focal plane located at the position of the laptop in FIG. 2A, and a compressed binary edge representative image derived from the confocal image.
Figure 2C:
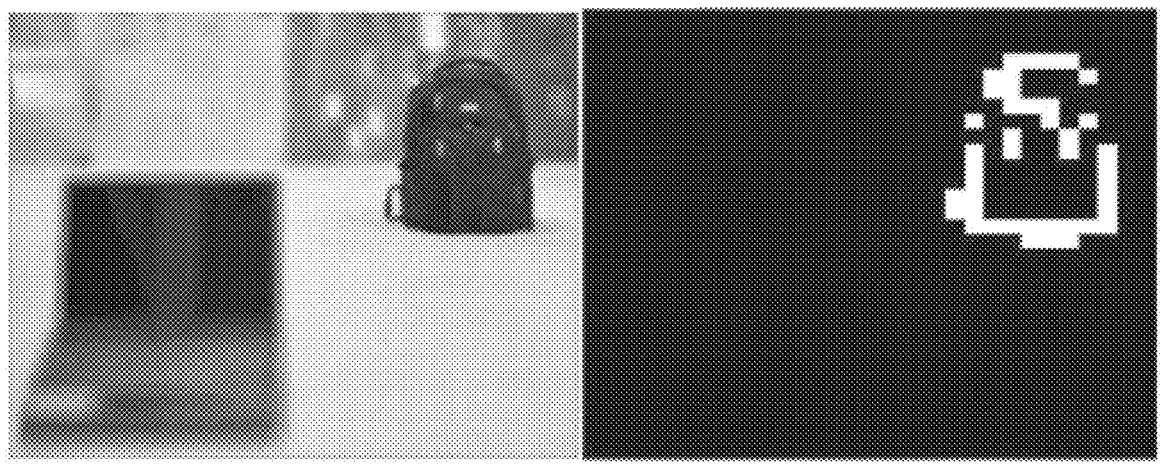
FIG. 2C is a confocal image corresponding to a focal plane located at the position of the backpack in FIG. 2A, and a compressed binary edge representative image derived from the confocal image.

FIGS. 2B and 2C show confocal images of the same scene taken with, for example, a light field camera, with focal depths of 1 m and 2 m, respectively. In the both confocal images, the target object at each focal depth is clearly focused, while contributions from background features and objects at other distances are blurred. When representative binary edge images (i.e., the right side images in FIGS. 2B and 2C) are produced by filtering and compression of the left images in FIGS. 2B and 2C, objects and features that constitute background clutter at the other depths are significantly suppressed. As a result, objects of interest at the selected focal depths within the representative images after compression are substantially easier to recognize.

Figures 3A, 3B, 3C:
FIG. 3A is a non-confocal image showing a bottle at a near distance from a camera and a complex background at a far distance from the camera.
FIG. 3B is a low-resolution compressed binary edge representative image derived from the non-confocal image of FIG. 3A.
FIG. 3C is a high-resolution compressed binary edge representative image derived from the non-confocal image of FIG. 3A.

FIGS. 3A-3F show a scene of a bottle in front of a complex background including several hanging wires on a lab bench. FIGS. 3A-3C show the scene without the use of confocal imaging. FIG. 3A shows an image of the scene captured by a conventional camera (492×327, 160,884 pixels). In the image, the camera focuses all objects within its depth-of-field. In the representative binary edge image shown in FIG. 3B, which is derived from FIG. 3A by binary edge filtering and compressing FIG. 3A down to a resolution of 38×25 pixels (e.g., using 950 binary electrodes of a visual prosthesis) and at binary levels, the bottle cannot be recognized in front of the complex background. In the higher resolution representative binary edge image shown in FIG. 3C, which is derived from FIG. 3A by binary edge filtering and compressing FIG. 3A down to a resolution of 70×47 pixels (e.g., using 950 binary electrodes) and at binary levels, the bottle still cannot be readily recognized even though the binary edge image has a higher resolution than the resolution of FIG. 3B.

Figures 3D, 3E, 3F:
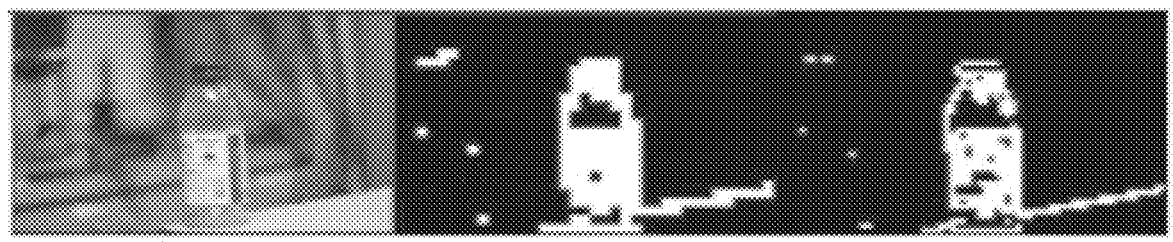
FIG. 3D is a confocal image showing a bottle at a near distance from a camera and a complex background at a far distance from the camera.
FIG. 3E is a low-resolution compressed binary edge representative image derived from the confocal image of FIG. 3D.
FIG. 3F is a high-resolution compressed binary edge representative image derived from the confocal image of FIG. 3D.

FIGS. 3D-3F show the scene with the use of confocal imaging. FIG. 3D shows an image generated with a narrow DOF lens, which simulates a confocal image. As shown in FIG. 3D, the bottle is focused while other depths in the image are blurred. As a result, the complex background is blurred. FIGS. 3E-3F, which are derived from FIG. 3D by binary edge filtering and compressing FIG. 3D down to resolutions of 38×25 pixels and 70×47 pixels, respectively, and at binary levels. At both the lower resolution confocal image of FIG. 3E and the higher resolution confocal image of FIG. 3F, the bottle is recognizable in front of the complex background. Background features—due to the confocal imaging technique—are suppressed, allowing the bottle in the representative binary edge images of FIGS. 3E-3F to be substantially easier to recognize.

FIG. 4A shows a schematic diagram of a blind user navigating through his or her environment, which includes an approaching pedestrian at a "near" distance, a tree at an "intermediate" distance, and a building at a "far" distance. Each of these objects is therefore positioned in focal planes at different distances relative to the position of the user within his or her environment. For example, the approaching pedestrian is approximately 1 m from the blind user; the tree is approximately 4 m from the blind user; and the building is approximately 9 m from the blind user. A conventional image of the user's environment is shown in the inset. In the left portion of the inset, the conventional image includes the approaching person, the tree, and the building all in focus. In the compressed, lower resolution binary representative image in the right portion of the inset, derived from the image in the left portion of the inset, the image of the person is difficult to distinguish due to interfering contributions from the tree and building, which are effectively background clutter. In the representative image, the approaching person is effectively masked by the tree and the building.

In contrast, the blind user "observes" the scene three-dimensionally using, for example, a visual prosthesis having a light-field camera with a lens array. The image information shown in FIG. 4B was obtained using a simulation of a two-dimensional micro lens array, with each lens in the array capturing an elemental image from a slightly different viewpoint. The three-dimensional image information allows visualization of objects or reconstruction of confocal images that correspond to specific depths of focus (e.g., distances from the blind user). In addition, whereas confocal imaging microscopy systems control focus through placement of apertures and thus capture only one distance (confocal image) per frame, the lens array can capture image information corresponding to focal planes at all distances (confocal images across the whole distance range) in one digital frame. The two insets show magnified 9×10 pixel subsets of the image information as an example. Each inset represents a different viewpoint captured by a different lens of the lens array. Each inset can be considered an elemental image of an array of elemental images that form the image information. The elemental images in the array can overlap. The lenses are positioned in different positions within the lens array and accordingly capture a different viewpoint of the scene.

Confocal images corresponding to a focal plane at any selected distance relative to the user can then be constructed rapidly from one frame of image information. Methods for constructing confocal images in this manner are disclosed, for example, in Stern, A., and Javidi, B., "Three dimensional sensing, visualization, and processing using integral imaging," *Proceedings of IEEE, Special Issue on 3D Technologies for Imaging and Display*, 94(3): 591-607 (2006), the entire contents of which are incorporated herein by reference.

Integral imaging using a light-field camera, as described above, yields an image that includes three-dimensional information about all objects that appear within the camera's field of view. This angular and spatial information is captured and encoded by the lens array; each lens of the array and the corresponding spatial region of the detector on which the lens directs light acts like an individual camera system. As a result, the light-field camera captures multiple perspective images corresponding to different camera positions. Each pixel of the light-field image is mapped to a particular angular direction by the lens array. While a light-field camera is described above, it should be understood other imaging or detection devices and sensors can be used to image the environment.

To generate individual confocal images corresponding to focal planes at specific distances from relative to the camera, the desired distance is first determined (as will be disclosed in greater detail later), and then each pixel of the light-field information is projected to the image plane at the selected confocal plane. On the image plane at the selected confocal plane, the distribution of pixels constructs the confocal image. If an object is located at the confocal plane, the distribution of pixels which contains the imaging information representing the object forms a focused image of the object. On the other hand, if an object is located outside of the confocal plane, contributions from the distribution of pixels are not condensed and remain sparse, producing a blurred image. After this simple pixel remapping and projection process, particular confocal images can be generated with simple summation calculation applied to the pixel intensity values.

Each constructed confocal image can include focused (sharp) and defocused (blurred) regions, depending on the actual distance of objects and features in the user's environment relative to the detector (and relative to the user, when the user wears or carries the detector). FIGS. 4C-4E show examples in which confocal images corresponding to different focal planes (e.g., different distances) are generated. The representative images of FIG. 4C-4E are confocal images computed using the image information shown in FIG. 4B, which is gathered by the lens array.

The upper image in FIG. 4C is a confocal image corresponding to a focal plane located at the "near" distance; the approaching pedestrian is in focus, while the tree and building are out of focus (e.g., blurred). Filtering and compression of the confocal left image yields the representative binary edge image (the lower image), in which the approaching pedestrian is readily distinguish while contributions (e.g., clutter) from the tree and building have been substantially suppressed.

Similar selectivity is demonstrated in FIGS. 4D and 4E. In FIG. 4D, the upper image is a confocal image corresponding to a focal plane located at the "intermediate" distance; the tree appears in focus, while the pedestrian and building are out of focus. The tree is partially occluded by clutter in front of the tree, such as the pedestrian. In the representative image generated from the confocal image and located below the confocal image in FIG. 4D, contributions from the approaching pedestrian and the building have been largely suppressed, and the tree is readily identified.

In FIG. 4E, the upper image is a confocal image corresponding to a focal plane located at the "far" distance; the building appears in focus, while the pedestrian and tree are out of focus.

In the corresponding representative image located below the confocal image in FIG. 4E, contributions from the approaching pedestrian and the tree have largely been suppressed, and the building is readily identified.

Zooming

FIG. 4F shows the effect of increasing the magnification (e.g., "zooming") of a confocal image prior to generating the representative image (e.g., a binary or bipolar edge representative image). In FIG. 4F, upon receiving an appropriate instruction from the user, the magnification of the confocal image (the upper image) is increased to increase the size of the approaching pedestrian in the image. When the representative image is generated from the magnified confocal image, the binary edge representation of the pedestrian is more detailed and even more recognizable. Contributions from the tree and building at other distances remain largely suppressed. The magnification of the confocal image (the upper image) of FIG. 4F creates a cropping of the image that is tighter than the corresponding confocal image of the approaching pedestrian shown in FIG. 4C. The representative image (the lower image) of FIG. 4F thus requires a lower level of compression (or, rather, a greater amount of pixels to represent the edges corresponding to the object of interest) than the representative image shown in FIG. 4C.

As shown in FIGS. 4A-4F, suppression of clutter and background contributions can effectively be achieved through the use of confocal imaging methods, and in particular, through the use of lens arrays to obtain three-dimensional image information about the user's environment, from which individual confocal images corresponding to focal planes at specific distances relative to the user's position can readily be constructed. In such confocal images, objects and features located at other distances are blurred due to defocusing. When representative images are generated from the confocal images, contributions from the blurred regions are reduced or even largely suppressed. A variety of different imaging systems can be used to obtain such light field image information. In particular, light field cameras from Lytro (Lytro Inc., Mountain View, Calif.) and Raytrix (Raytrix GmBH, Kiel, Germany) can be used. Other imaging system can also be used to obtain confocal images.

The effect of zooming is further shown in FIGS. 5A-5C, which shows representative images of an object of interest—a backpack. In FIG. 5A, a representative image generated by binary edge filtering is a high resolution confocal image that shows a relatively high level of detail. The representative image of FIG. 5A has a resolution of 327×327 pixels. When the image is subsequently compressed as shown in FIG. 5B, some resolution and detail are lost. The representative image of FIG. 5B has a resolution of 33×33 pixels. The backpack in the representative image spans approximately 25% of the available pixels of the representative image. However, when the image of FIG. 5A is first zoomed to magnify the object of interest and then compressed, more detail is preserved following compression. The backpack in the representative image of FIG. 5C occupies a greater proportion of the representative image. The representative image of FIG. 5C thus shows a greater amount of detail of the backpack than the representative image of FIG. 5B.

Confocal Image Generation, De-Cluttering, and Compression Using Bipolar Edge Filtering In some implementations, a visual prostheses can support more than a binary level of pixel representation. The binary edge filtering described above uses a binary level to represent each pixel in the representative image. In multi-level bipolar edge filtering, for example a modified version of the Laplacian of Gaussian (LoG) filtering followed by bipolar threshold and resulting in bipolar multi-level edge representation can be used to provide greater detail in an image of a scene. The bipolar edge filtering technique provides information about which side of an edge of the object depicted is dark and which side of the edge is bright.

In bipolar edge filtering, the LoG filtering can be used to remove areas of blurred content in the confocal image, as used in the binary edge filtering technique described above. Zero-crossing positions in the filtered confocal image can indicate a location (e.g., an edge of the object of interest) in the filtered confocal image corresponding to where the image intensity gradient starts increasing or starts decreasing. A zero-crossing position generally corresponds to when an intensity of the image changes sign (goes from positive to negative or negative to positive). As a result, the zero-crossing positions (e.g., the edge of the object of interest) can be marked as having a dark pixel (e.g., negative) and a bright pixel (e.g., positive) against grey pixels for the background. The dark and bright pixels can indicate the brightness change that occurs across the edges of the object of interest. Thus, bipolar edge filtering indicates which side of an edge is bright and which is dark. The binary edge filtering described above cannot distinguish between cusps and simple edges of the object of interest. With bipolar edge filtering, cusps can be distinguished from edges, as the cusps have a single polarity, while the edges have two polarities. While the above method describes a specific implementation of bipolar multi-level edge filtering, in other implementations, other methods of bipolar multi-level edge filtering can be used.

In the image of FIG. 6A, a detector (e.g., a light-field camera) generates a confocal image of a scene with a desk lamp in front a complex background. FIG. 6B shows a representative image of the scene using the edge filtering and compressing described above with respect to, for example, FIGS. 3B-3C, 3E-3F, and 4C-4E. FIG. 6B is a compressed representative image of FIG. 6A in which the scene of the desk lamp is shown at a resolution of 38×25 pixels. In the image of FIG. 6C, a bipolar edge filtering provides an image of 492×327 pixels with three grey levels for each pixel. Contrast polarity (e.g., a dark pixel, a bright pixel, and a grey background pixel) occurs for the straight edges of the desk lamp, and single polarity (e.g., a dark pixel and a grey background pixel, or a bright pixel and a grey background pixel) is used for several of the cusps of the desk lamp. FIG. 6D shows a compressed image of FIG. 6C in which the scene of the desk lamp is shown at a resolution of 38×25 pixels with three grey-levels for each pixel. FIG. 6D has the same resolution of FIG. 6C but provides greater detail in the geometry of the desk lamp due to the use of an additional grey level to represent the edges of the desk lamp in the representative image.

While the above example describes a 3-level dynamic range, additional level dynamic ranges are possible. For example, a 4-level dynamic range could be implemented into a bipolar multi-level edge filtering technique. In some implementations, two or more levels can code for the background. In some cases, the bipolar edges can be represented as having more than one level of brightness/darkness, depending on the number of levels of the dynamic range.

Automatic Detection of Confocal Distance of Objects of Interest

In some embodiments, the system 100 can automatically determine confocal distances of objects of interest by scanning several confocal planes of a scene. In general, for each confocal plane (or confocal image), the system 100 can compute the number of pixels that are in focus. The system 100 can then determine a plane at a first confocal distance likely has an object of interest if the number of focused pixels in that plane is greater than the number of focused pixels in other planes having a confocal distance near the plane at the first confocal distance. The algorithm for automatic detection of confocal distances of objects of interest is described in more detail below.

The confocal planes can be generated using the methods described above. Each confocal plane has a confocal distance spaced apart from adjacent planes. In some cases, the step size between confocal planes is 30 mm such that the distance between adjacent confocal planes is 30 mm. In other implementations, the step size can be, for example, 10 mm, 100 mm, or more. In some implementations, the step size can vary as the imaging system scans deeper areas of the scene. For example, up to 2 meters of depth, the step size can be 30 mm. After 2 meters, the imaging system can increase the step size to 60 mm to reduce the number of confocal images that need to be captured. The step size can be nonlinearly increased by the distance from the system.

Focused edge regions of each confocal image can correspond to edges of objects of interest. These edges can be enhanced in order to distinguish them from the blurred regions of the confocal image. Edge regions of each confocal plane can be enhanced and detected using an edge enhancement and detection operation. For example, the edge enhancement and detection operation can implement a gradient-like operation (in three directions) obtained using the first-scale Haar wavelet transform. Then, with an adaptive threshold in each sub-band of the wavelet, the edge locations in greatest focus can be detected. As the threshold applied to the wavelet sub-band is decreased, the number of detected edge pixels is increased. In the adaptive process, the threshold is adjusted to set the number of detected edge pixels to 0.5% of all pixels in the sub-band. Methods to enhance edge regions are further described in Mallat, S. G., "Multifrequency channel decompositions of images and the wavelet models," published in 1989 (IEEE, 37(12), 2091-2110) and Aloni & Yitzhaky, "Detection of object existence from a single reconstructed plane obtained by integral imaging, (IEEE Photonics Technology Letters, 26(7), 726-728) (2014), the contents of which are incorporated herein in their entireties.

To determine the depth of objects in the light-field image, the edge enhancement and detection operation is repeated for confocal planes at several confocal distances. A non-confocal image is also generated, and the edge enhancement and detection operation is applied to the non-confocal image. Then, for each confocal distance, the number of edge pixels in each confocal plane that overlap with edge pixels of the non-confocal is counted. As the edge pixels have been enhanced using the edge enhancement and detection operation described above, a fraction of overlapping edge pixels (e.g., the fraction of edge pixels in the confocal image that overlap with the edge pixels in the non-confocal image) can generally correspond to a proportion of the confocal image that is in focus. A fraction of overlapping edge pixels is expected to achieve local maxima at depth planes that contain objects because objects at these planes appear sharp in both the confocal planes and the non-confocal image, thus producing edges at similar locations. Edge pixels at blurred planes are either suppressed or shifted slightly and thus do not overlap with the sharp edges in the image, resulting in a smaller number of intersecting edge pixels for the blurred planes.

Referring to FIGS. 7A-7I, a scene having a camera and a mug in front of a background is captured. FIGS. 7A-7C correspond to a non-confocal image, a representative non-confocal binary edge image of the non-confocal image, and an enhanced representative non-confocal binary edge image of the representative non-confocal binary edge image, respectively. FIGS. 7D-7F show images at a first confocal distance of approximately 0.6 m, which allows the mug and the camera to be in focus in the corresponding images. FIGS. 7D-7F correspond to a first confocal image at a first confocal distance, a first representative binary edge image of the first confocal image, and a first enhanced representative binary edge image of the first representative binary edge image, respectively. FIGS. 7G-7I show images at a second confocal distance of approximately 3 m, which allows the background to be in focus in the corresponding images. FIGS. 7G-7I correspond to a second confocal image at a second confocal distance, a second representative binary edge image of the second confocal image, and a second enhanced representative binary edge image of the second representative binary edge image, respectively. The first enhanced representative binary edge image and the second enhanced representative binary edge image can be compared to the enhanced representative non-confocal binary edge image. A fraction of overlapping edge pixels can be computed for both the first and second enhanced representative binary edge images (as described above). The fraction can be computed for several confocal distances. Referring to FIG. 7J, a graph of the fraction of overlapping edge pixels at various confocal distances is shown. At 0.6 m and 3 m, which correspond to the first and second confocal distances, respectively, local maxima of the fraction of overlapping edge pixels occur. These local maxima represent the confocal planes having objects of interest as determined by the automatic detection algorithm described above. The method for automatic detection of confocal distance to objects of interest can other blur metrics known in the art.

Active Operation Modes

In certain embodiments, instead of selecting specific focal plane distance values, the user selects a mode of operation of system 100. The system's mode of operation defines focal plane distance values either as specific values (e.g., distances) relative to the position of the user, or as ranges of values relative to the user's position and bounded by upper and/or lower limits. In some cases, the user selects the mode of operation and interacts with the environment through the prosthesis settings that user selects. The user can interact manually with the environment by scanning vertically or laterally by, for example, moving a head of the user or a hand of the user. The user can also zoom in on detected or selected objects using the methods described above. In other implementations, a computer selects the mode of operation. As will be described below, modes of operation can include a free-search mode, a confocal-extension mode, and an obstacle-avoidance mode.

Free-Search Mode

The system 100 can operate in a free-search mode, which can be useful for, for example, orientation. In this mode, several distance values are predefined or selected by the system, and information about objects that appear in focus at focal planes corresponding to the distance values is made available to the user to explore. The user can then select one or more depth planes for further investigation, exploring the set of distances values which correspond to the object(s) of interest. The user can also provide instructions to select specific regions of the confocal images to effectively magnify or "zoom" the object(s) of interest for improved identification and to scan laterally across the environment.

Figure 8A:
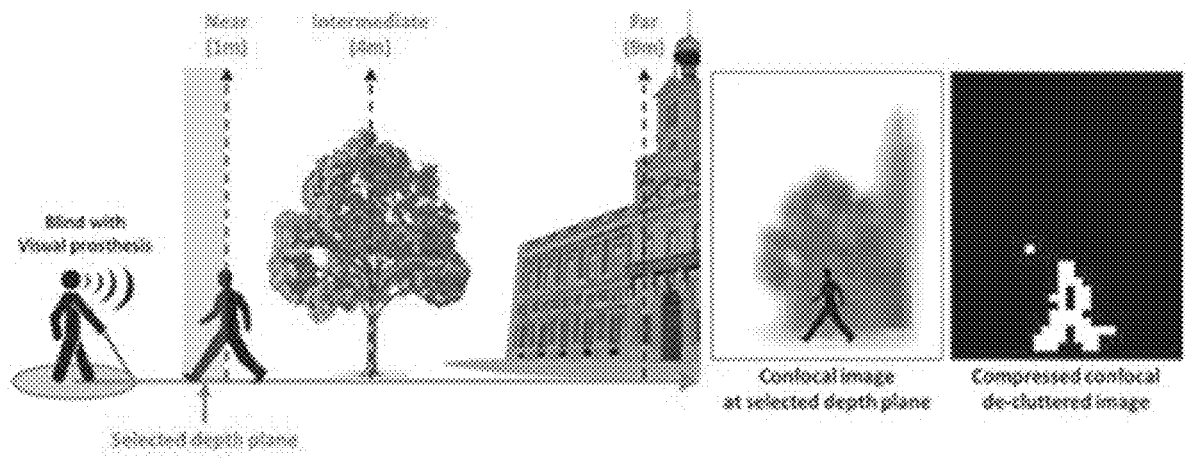
FIG. 8A is a schematic diagram showing a free-search mode of operation of an active confocal imaging system.

Referring to FIG. 8A, a user can freely select a depth plane. The user selects the depth plane corresponding to approximately 1 m, where an approaching person is located. The system 100 produces the confocal image at the selected depth plane. The system 100 then implements binary edge filtering and compression and shows a de-cluttered representative image at the selected depth. The representative image shows a representation of the approaching person. The user can freely select depth plane. In some implementations, depth plane selection can be available continuously from all planes or from a limited selection of planes automatically isolated for including a potential object of interest. For example, in FIG. 8A, the system 100 can restrict the depth plane selection to the depth planes where the potential objects of interest are located (e.g., 1 m depth plane for the approaching person, 4 m depth plane for the tree, and 9 m depth plane for the building).

In other embodiments, in free-search mode, the system scans through focal planes at various distances relative to the position of the detector/user to automatically select and focus on a small number of distance values (e.g., 4 to 5) that contain objects. The user can switch between focal planes in active visual exploration by issuing appropriate instructions to system 100 through the input interface, and can optimize resolution using zoom capability as described above. This approach is similar to the way the human active vision system functions. In other implementations, a controller is mounted on a long cane. A user could use the controller to isolate and then zoom in on one of several objects selected automatically from the image obtained by, for example, a head-mounted camera. To reduce the scanning time required by the user, the free-search mode can include automatic detection of planes that may contain objects of interest, as described in detail above.

Confocal-Extension Mode

Figure 8B:
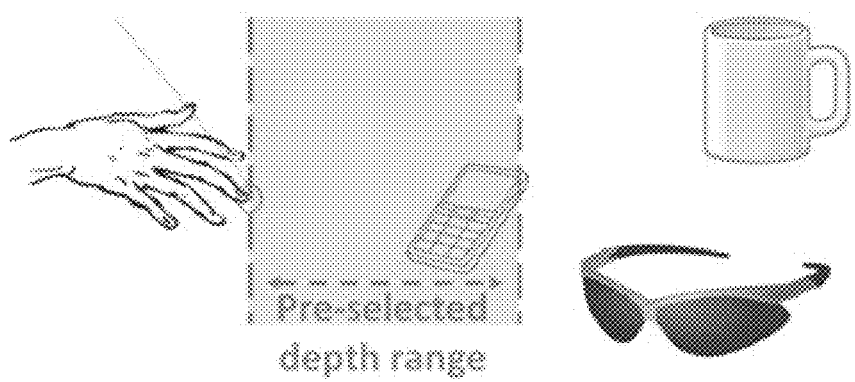
FIG. 8B is a schematic diagram showing a confocal-extension mode of operation of an active confocal imaging system.

In a confocal-extension mode, the system 100 detects the location of an arm or cane of the user and selects a range of confocal depths that encompasses the location of the arm or cane. The confocal-extension mode can be used to locate objects that are just beyond the reach of the user's hand or long cane. This mode defines a range of distance values bounded by a lower limit that corresponds to the maximum extension of the user's current hand or cane position. In this mode of operation, the system provides information only about the portions of the user's environment positioned at distances he or she cannot manually reach. Referring to FIG. 8B, as a user probes an area containing a cellular phone, sunglasses, and a mug, the system 100 locates the hand of the user and selects a range of depths available to the user based on the location of the hand. The system 100 then presents to the user a view of the range. In some implementations, the narrow range is beyond the location of the hand by, for example, 20 cm. In FIG. 8B, the system 100 presents a confocal image of the depth range containing the cellular phone to the user because the cellular phone is immediately ahead of the hand of the user. The confocal-extension mode can allow the user to find and grasp objects within reach of the hand or, in some cases, find and above objects in immediate reach of the hand before touching the objects. While the system 100 has been described to detect the hand or the cane to select a confocal depth, in other implementations, the system may select a depth after detecting any body part of the user.

Obstacle Avoidance Mode

In the obstacle avoidance mode, the system 100 displays only objects that enter a pre-selected depth range from the position of the user and will alert the user when an object is detected within the depth range. The obstacle avoidance mode indicates to the user obstacles or hazards that are missed or not reachable by a cane. Objects that fall within the depth of focus around the selected distance values represent potential hazards for the user, who must navigate around them or otherwise avoid collision with them as they approach closely to the user. In addition to providing representative images of such objects to the user, system 100 can also issue one or more warning signals (e.g., haptic signals and/or auditory signals) to alert the user.

Figure 8C:
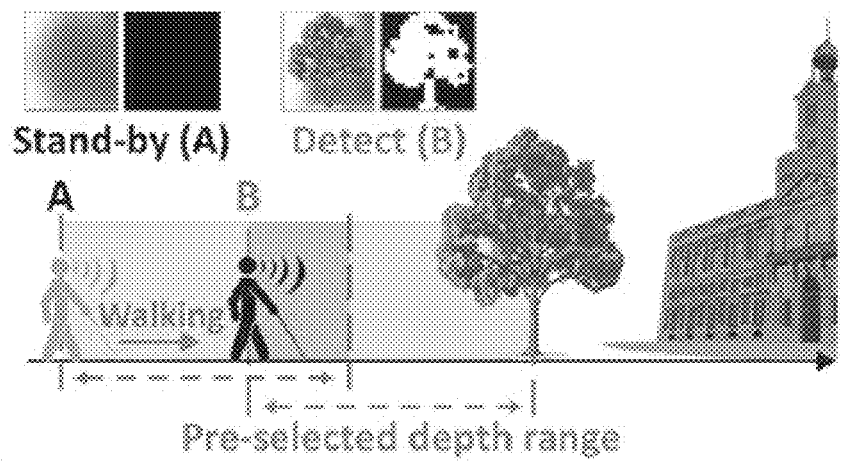
FIG. 8C is a schematic diagram showing an obstacle-avoidance mode of operation of an active confocal imaging system.

Referring to FIG. 8C, the pre-selected depth range changes as the user moves from position A to position B. When the user stands at position A, the system 100 does not detect an obstacle because the tree is outside of the pre-selected depth range defined by the obstacle-avoidance mode of operation. As shown in the upper left inset to the figure, the tree appears blurred in confocal images that correspond to distance values that correspond to the operating mode. In the corresponding representative image to the left of the confocal image, contributions due to the approaching person are largely suppressed. It means the user has no obstacle within selected range. When the user arrives at position B, the system 100 detects the tree as a potential obstacle and can alert the user. As shown in the confocal image of the upper right inset, the tree is focused and readily identified. The corresponding representative image shows a distinct outline of the tree. When an obstacle (e.g., the tree) is detected, the user can execute an avoidance maneuver based on the representative image produced by the system 100. In some cases, the operation mode of the system can automatically switch to a mode more suitable to for a situation for the user.

Methods of Use

Figure 9:
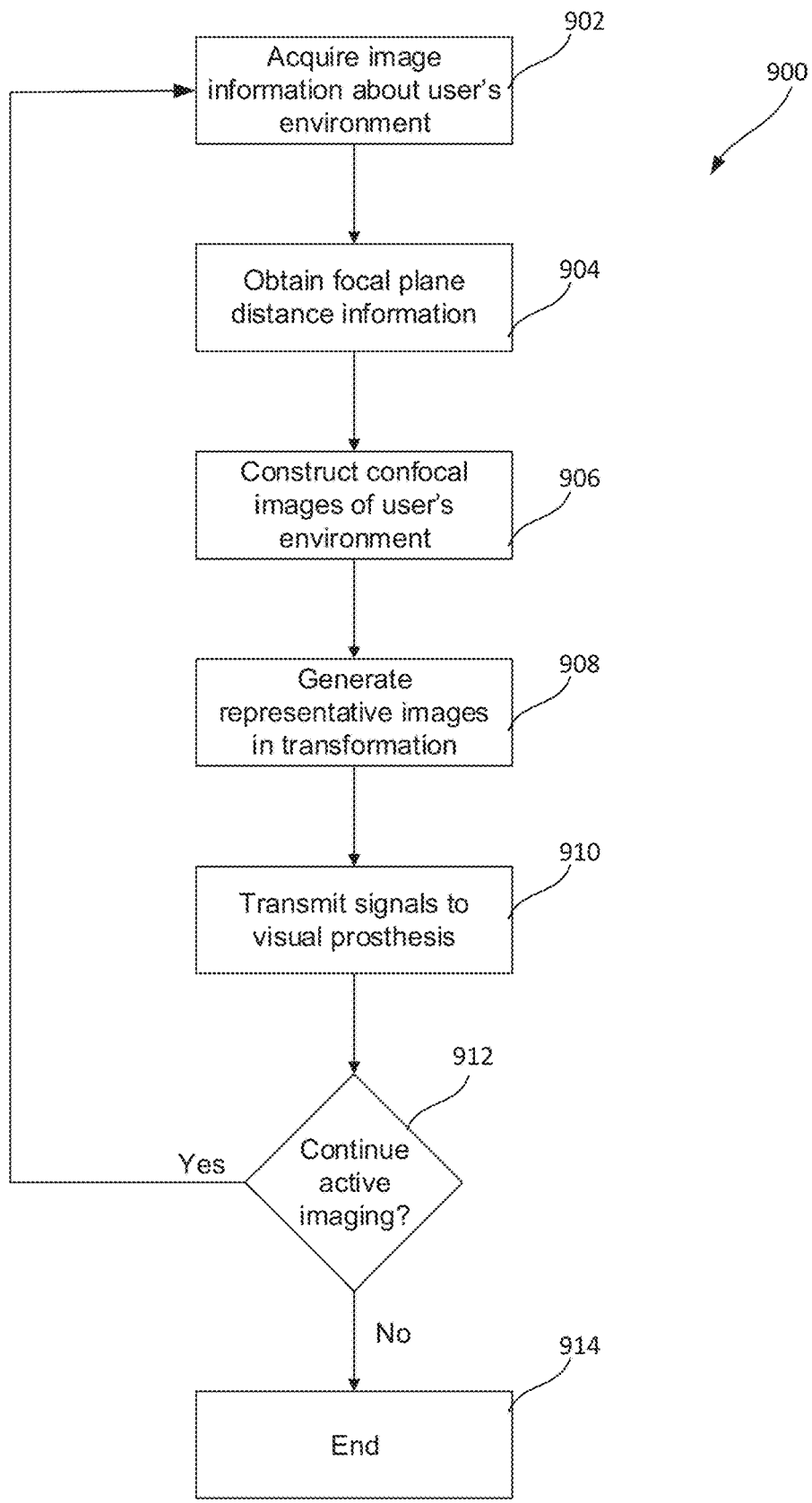
FIG. 9 is a flow chart showing a series of steps for delivering information about a user's environment to the user.

FIG. 9 shows a flow chart 900 that includes a series of steps for delivering information about a user's environment to the user. In the first step 902, three-dimensional image information about the user's environment is acquired. Methods for acquiring this information are discussed above and can include, for example, using a two-dimensional array of lenses to focus individual images—each corresponding to a slightly different perspective—onto different regions of a detector.

Next, in step 904, focal plane distance information is obtained. The focal plane distance information defines a set of one or more distance values associated with the user's environment and relative to the user's position. The distance values are then used to determine which confocal images are constructed. Distance information can be obtained in a variety of ways. In some embodiments, for example, distance information can be stored in a storage or memory unit within system 100 and accessible by processor 106. In some embodiments, distance information can be obtained from the user of system 100. For example, the user can manually select one or more focal planes corresponding to different distances by activating controls on input interface 110, and/or by issuing a speech command that is detected by input interface 110 and recognized by processor 106. In other embodiments, the focal plane distance information is selected based on the selected mode of operation (e.g., the free-search mode, the confocal-extension mode, or the obstacle avoidance mode) as described above.

After the focal plane distance information has been obtained, one or more images of the user's environment are constructed in step 906 based on the focal plane distance information. As discussed above, the one or more images are typically confocal images, which can be constructed in various ways depending upon the nature of the image information acquired in step 402. For example, where the image information is acquired using a lens array, the one or more confocal images can be constructed by combining pixel intensity values from different spatial regions of the image information. Where the image information is acquired as a series of confocal images each corresponding to a focal plane at a specific distance relative to the detector/user, constructing the images of the user's environment can include selecting a subset of the confocal images from the set.

Next, in step 908, representative images are generated from the confocal images of step 906 by transforming the confocal images. A variety of different transformations can be applied to the confocal images to generate the representative images. In general, the representative images have reduced dynamic range and reduced resolution relative to the confocal images. In some cases, the representative images are produced using binary edge filtering techniques, as described herein. In other cases, the representative images are produced using bipolar multi-level edge filtering techniques described herein.

In some embodiments, confocal images are transformed by using edge detection algorithms to generate the representative images. Suitable edge detection algorithms are disclosed, for example, in Aloni & Yitzhaky, "Detection of object existence from a single reconstructed plane obtained by integral imaging, (IEEE Photonics Technology Letters, 26(7), 726-728)(2014), the entire contents of which are incorporated herein by reference.

In certain embodiments, confocal images are transformed by using quartertone and or halftone conversion and/or adaptive thresholding. Suitable algorithms for implementing such techniques are disclosed, for example, in: Goldstein, Peli, and Wooledge, "Medical image communication using halftone algorithms," *Proceedings of the Society of Photo-Optical Instrumentation Engineers* 845: 413-418 (1987); Peli and Lahav, "Drusen measurements from fundus photographs using computerized image analysis," *Ophthalmology*, 93(12), 1575-1580 (1986); and Peli, "Simple 1-D enhancement for head-mounted low vision aid," *Visual Impairment Research* 1(1): 3-10 (1999). The entire contents of each of the foregoing references are incorporated herein by reference.

In some embodiments, temporal averaging can be used to generate the representative images. Temporal averaging is akin to what happens with head mounted cameras of vision prostheses. In actual prosthesis use, small head position changes (head tremor) cause a slightly different image of the same object to be acquired in every frame. Because of imaging noise, quantization noise, and other effects of the processing, this results in a slightly different compressed image representation generated for every frame. The perception of these similar images is averaged by the "visual" system, effectively resulting in less noise and higher resolution, as well as perceived higher dynamic range. The effect is similar to the stochastic resonance effect demonstrated for tactile displays and other modalities. When produced by jitter, it was recently shown to improve performance by patients with AMID and particularly improves quality of low-resolution edge images. Such temporal averaging methods can be used in step 908 to generate one or more of the representative images.

Next, in optional step 910, one or more signal can be transmitted to a visual prosthesis worn by the user or embedded within the user's eye. As discussed above, the representative images generated in step 908 can be converted to electrical signals that are compatible with retinal implants or other types of prostheses, and the electrical signals can be delivered to the prostheses (e.g., via signal transmitter 108). Similar signals can also be delivered to other sense organs serving the prosthesis such as the skin and/or the tongue, for example. The visual prosthesis can have electrodes configured to provide binary signals or bipolar multi-level signals (e.g., three levels, four levels, or more).

In decision step 912, if imaging of the user's environment is complete (e.g., if the user de-activates system 100), then the procedure ends at step 914. Alternatively, if system 100 operates continuously to provide updated information to the user, then process control returns to step 902.

The systems disclosed herein can serve as a front end imaging system for any of a variety of existing retinal implants, visual prostheses, and sensory substitution devices (SSDs) envisioned today, and with minimal adjustment or tuning, substantially improving the user's recognition performance. With current prosthetic systems, users typically require very long times to interpret images. The systems disclosed herein reduce interpretation times significantly and at the same time, permit active exploration of the user's environment.

Typically, system 100 is worn or carried by the user to enable navigation within, and interaction with, the user's environment. In some embodiments, system 100 is configured to be wearable, and is partially or fully integrated into one or more articles of clothing or other wearable apparatus.

Figure 10A:
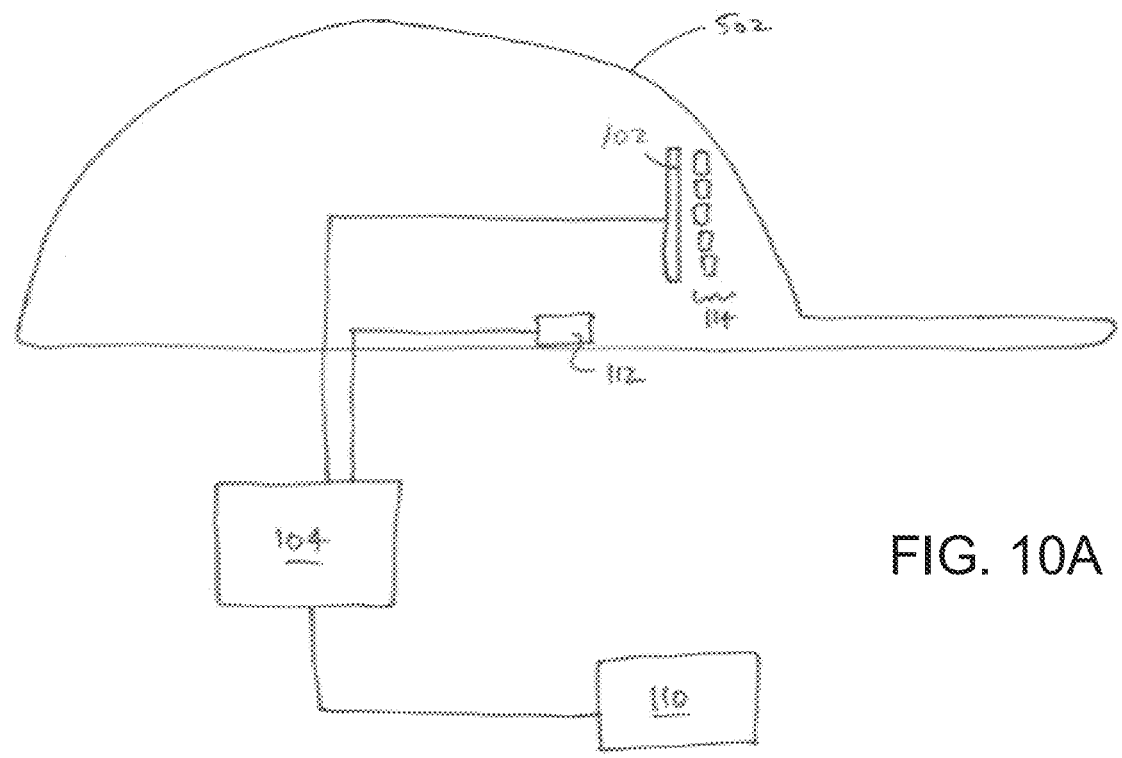
FIG. 10A is a schematic diagram showing an active confocal imaging system partially integrated into a hat.

In certain embodiments, system 100 is implemented as a head-mounted apparatus. FIG. 10A shows one embodiment of a head-mounted apparatus in which certain components of system 100 are integrated into a hat 502 worn by the user. In particular, lens array 114 and detector 102 are positioned in a front portion of the hat, while output device 112 is positioned in a lateral portion of hat 502. In some embodiments, control unit 104 can be positioned within hat 502 as well, and connected to detector 502 to provide operating power for the detector. In certain embodiments, as shown in FIG. 10A, control unit 104 can be worn on another part of the user's body (e.g., at the waist) and is connected to detector 102 via a wired or wireless connection. In addition, the system can be added on accessories such as, for example, a cane, a ring, a bracelet, a necklace, a pin, a pendant, and/or gloves.

Input interface 110 can be connected directly to control unit 104 and worn in a location proximate to control unit 104 to allow the user to send instructions and issue commands to control unit 104. In certain embodiments, input interface 110 can be positioned on another article (e.g., integrated into the handle of a long cane) and can be connected to control unit 104 via a wired or wireless connection.

Figure 10B:
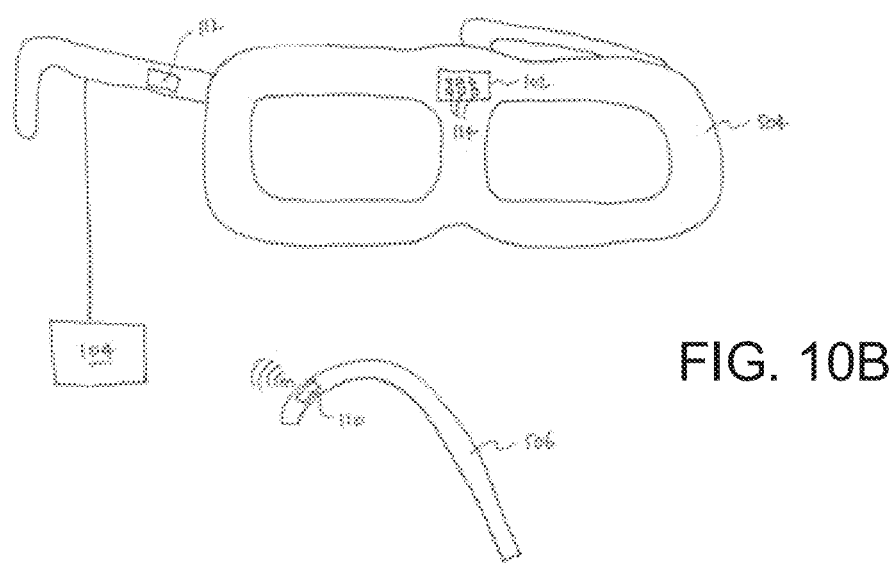
FIG. 10B is a schematic diagram showing an active confocal imaging system partially integrated into eyeglass frames.

Another head-mounted implementation is shown in the schematic view of FIG. 10B, in which lens array 114, detector 102, and output device 112 are integrated into eyeglass frames 504. Detector 102 and output device 112 are connected to control unit 104 through the eyeglass frames, and control unit 104 is configured to worn at the waist of the user as described above. Input interface 110 is integrated into the handle of cane 506, and is wirelessly connected to control unit 104.

Hardware and Software Implementations

The steps described herein can be implemented in computer programs using standard programming techniques. Such programs are designed to execute on programmable computers or specifically designed integrated circuits, each comprising an electronic processor (e.g., processor 106), a data storage system (including memory and/or storage elements), at least one input device, and least one output device, such as a display or printer. The program code is applied to input data (e.g., three-dimensional image information and/or confocal images) to perform the functions described herein and generate output signals and/or information. Each such computer program can be implemented in a high-level procedural or object-oriented programming language, or an assembly or machine language. Furthermore, the language can be a compiled or interpreted language. Each such computer program can be stored on a tangible, physical computer readable storage medium (e.g., USB memory, CD ROM or magnetic diskette) that when read by a computer or electronic circuit can cause the processor in the computer or circuit to perform the analysis and control functions described herein.

Example

In the example described below, the impact of background de-cluttering on object recognition using confocal images is shown.

Six normally sighted subjects (3 female, 3 male, ages 24 to 42) were tested to determine the recognition rates of 20 randomly ordered objects (office and household items), with and without background de-cluttering. The background de-cluttered condition corresponds to the application of the confocal image generation, de-cluttering, and compression (using binary edge filtering) algorithms described herein. The 20-object images were randomly ordered within blocks of the same compression level and same background condition (cluttered versus de-cluttered). Confocal imaging was simulated by a narrow DOF camera and then edge filtering was applied for de-cluttering. The de-cluttered image set was presented to the subjects at 8 different levels of resolution (simulating different electrode densities); 12×8 (96), 27×18 (486), 38×25 (950), 70×47 (3,290), 98×65 (6,370), 164×109 (17,876), 246×164 (40,344), and 492×327 (160, 884 electrodes); in that order, with fixed 10×7° Field of View (FOV).

For each subject, the presentation of a block of images started from low resolution and proceeded to higher resolution. At each compression level, randomly ordered presentations of the background-cluttered images of 20 objects were followed by a block of background de-cluttered images. This sequence of 320 images was displayed on a 2100 P1130 Trinitron® CRT monitor (Dell Inc., Round Rock, Tex.) at 1280×1024 resolution and observed by subjects from 80 cm away. The size of all images was 14.6 cm by 9.7 cm, spanning a visual angle of 10.4°×6.9°. The image sequence was displayed at the center of the screen surrounded by a blue border so that subjects could easily distinguish the area of the image.

The results show that the recognition rate with the background de-cluttered condition was higher than with the background cluttered condition at all resolutions. In particular, the background de-cluttering increased the objects' recognition rate by a factor of 5.6.

Figure 11A:
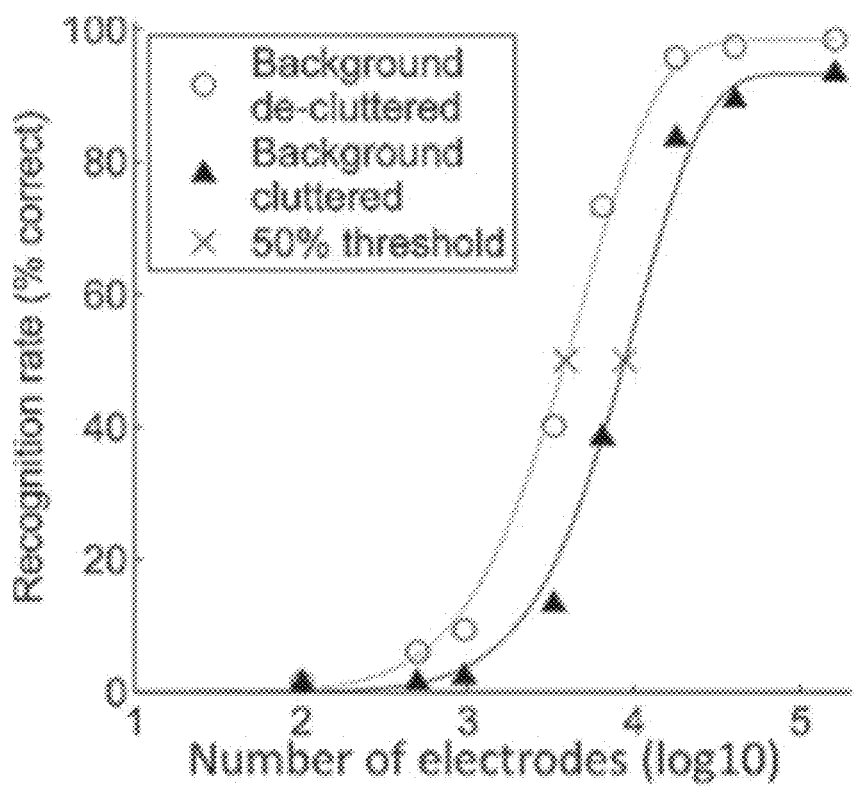
FIG. 11A is a graph of experimental results showing recognition rate of objects measured against a number of electrodes in a visual prosthesis with and without use of an active confocal imaging system.
Figure 11B:
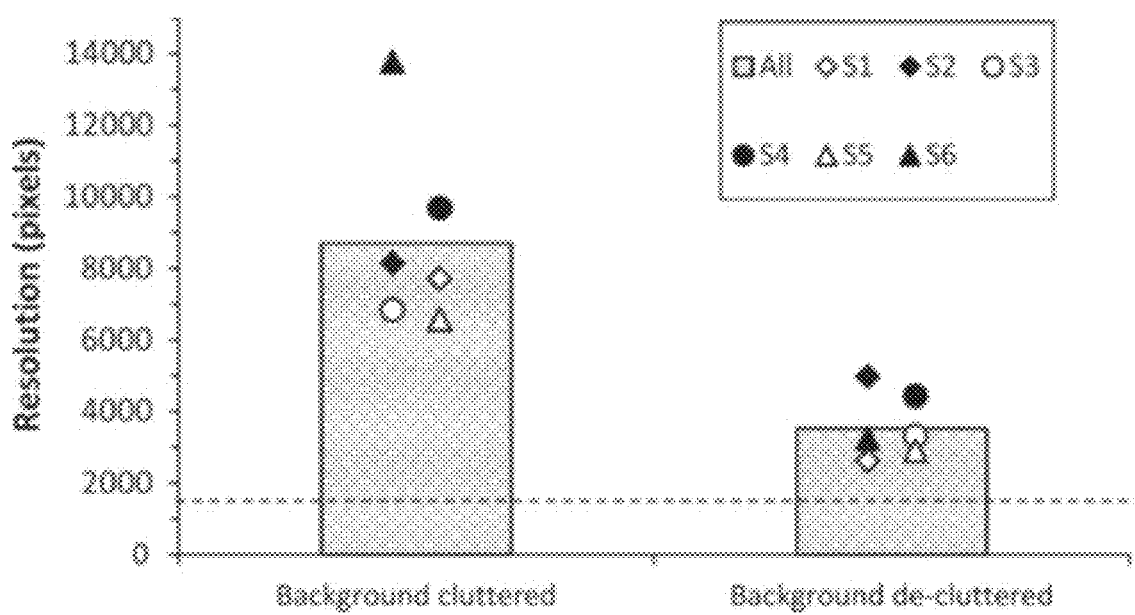
FIG. 11B is a graph of the experimental results of FIG. 11A showing resolutions resulting in a 50% recognition rate of objects with and without use of an active confocal imaging system.

FIG. 11A is a graph of the number of electrodes in the visual prostheses versus the recognition rate for a background cluttered condition and a background de-cluttered condition. FIG. 11B reproduces the results of FIG. 11A in the form of a bar graph. FIG. 11B shows the resolution that resulted in a 50% recognition rate for each subject under background cluttered and de-cluttered conditions. The dashed line (at 1,500 pixels) serves as a baseline for resolutions of conventional visual prostheses.

FIGS. 11A and 11B show that the 50% recognition threshold for the conventionally-compressed edge images occurred when the resolution was 8,695 pixels (about 114× 76), while, for the de-cluttered images, the same 50% performance was achievable at a resolution of 3,532 pixels (about 73×48). The recognition rates around the resolutions of current visual prostheses ($10^2$ to $10^3$ electrodes) were under 15% in both conditions. When the compressed resolution was higher than 31,000 pixels, subjects could recognize most objects regardless of the background condition. For resolutions lower than 100 pixels, most objects could not be recognized by subjects regardless of background condition. With the 1,000 to 10,000 pixel resolutions targeted, the recognition rates were improved by de-cluttering.

OTHER EMBODIMENTS

A number of embodiments have been described. Nevertheless, it will be understood that various modifications may be made without departing from the spirit and scope of the disclosure. Accordingly, other embodiments are within the scope of the following claims.

What is claimed is:

1. A system for providing information to a user about an environment, the system comprising:
   an electronic processor configured to perform operations comprising:
      receiving image information about the environment, the image information being indicative of focal plane distance information defining a set of one or more distance values relative to the user within the environment, and
      generating, based on the image information and the focal plane distance information defining the set of one or more distance values, one or more representative images representative of one or more confocal images of the environment, wherein each of the one or more representative images corresponds to a corresponding one of the one or more confocal images; and
   a transmitter connected to the electronic processor and configured to transmit a signal comprising information corresponding to the one or more representative images to an output device.

2. The system of claim 1, wherein the operations further comprise determining an operating mode associated with the system, and
   wherein receiving the image information comprises receiving the image information based on the operating mode associated with the system.

3. The system of claim 2, wherein the operations further comprise initiating the operating mode, the operating mode being at least one of a free-search mode, a confocal extension mode, and an obstacle avoidance mode, wherein, in the free-search mode, the focal plane distance information is selected by the user, wherein, in the confocal extension mode, the focal plane distance information is selected based on a location of a body part of the user, and wherein, in the obstacle avoidance mode, the focal plane distance information is a pre-selected depth range from the user.

4. The system of claim 1, wherein receiving the image information comprises receiving multiple portions of the image information that correspond to images formed by different lenses arranged in an array.

5. The system of claim 1, wherein the one or more confocal images comprise at least 3 confocal images.

6. The system of claim 1, wherein the focal plane distance information comprises a range of distance values bounded by a minimum distance value.

7. The system of claim 1, wherein the focal plane distance information comprises a range of distance values bounded by a maximum distance value.

8. The system of claim 1, wherein the one or more confocal images comprise halftone edge images.

9. The system of claim 1, wherein the signal comprising the information corresponding to the one or more representative images comprises an electrical signal, and the transmitter is configured to transmit the signal to a visual prosthesis worn by the user.

10. The system of claim 1, further comprising an input interface configured to receive input information from the user and to transmit the input information to the electronic processor, the input interface comprising a controller mounted to a cane.

11. The system of claim 1, further comprising an input interface configured to receive input information from the user and to transmit the input information to the electronic processor, the input interface comprising a voice-activated interface.

12. The system of claim 1, wherein each of the one or more representative images comprises fewer pixels and a lower dynamic range than a set of pixels and a dynamic range of the corresponding one of the one or more confocal images.

13. A system for providing information to a user about an environment, the system comprising:

an output device to present, to the user, a representation of the environment, the representation being representative of one or more confocal images of the environment and generated based on focal plane distance information defining a set of one or more distance values relative to the user within the environment; and a user input device operable by the user to determine the focal plane distance information.

14. The system of claim 13, wherein the user input device is operable by the user to initiate an operating mode in which the focal plane distance information is determined.

15. The system of claim 14, wherein the operating mode comprises a free-search mode, wherein the user input device is operable, in the free-search mode, to determine the focal plane distance information in response to a user selection of a distance value associated with the focal plane distance information, the distance value selected from multiple predefined distance values.

16. The system of claim 15, wherein the user input device is operable by the user to select a specific region of the representation, and wherein the output device presents a magnified representation of the specific region of the representation.

17. The system of claim 15, wherein the multiple predefined distance values are associated with focal planes containing potential objects of interest.

18. The system of claim 14, wherein the operating mode comprises a confocal-extension mode, wherein the user input device is operable, in the confocal-extension mode, to detect a location of a hand of the user, and wherein the representation is representative of a view of a range of depths relative to the user available to the hand of the user.

19. The system of claim 14, wherein the operating mode comprises an obstacle avoidance mode, wherein the system is configured to provide an alert to the user in response to an obstacle being within a depth range relative to the user.

20. A method for providing information to a user about an environment, the method comprising:

receiving image information about the environment, the image information being indicative of focal plane distance information defining a set of one or more distance values relative to the user within the environment, and generating, based on the image information and the focal plane distance information defining the set of one or more distance values, one or more representative images representative of one or more confocal images of the environment, wherein each of the one or more representative images corresponds to a corresponding one of the one or more confocal images; and transmitting a signal comprising information corresponding to the one or more representative images to an output device.

* * * * *

UNITED STATES PATENT AND TRADEMARK OFFICE
CERTIFICATE OF CORRECTION

PATENT NO. : 10,857,036 B2
APPLICATION NO. : 16/183930
DATED : December 8, 2020
INVENTOR(S) : Eliezer Peli and Jae-Hyun Jung Page 1 of 1

It is certified that error appears in the above-identified patent and that said Letters Patent is hereby corrected as shown below:

In the Specification

In Column 1, Line 19, delete "NIH grant number R01EY05957" and insert -- Grant Number EY005318 awarded by the National Institutes of Health --

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*